US010336749B2

(12) United States Patent
Platzek

(10) Patent No.: US 10,336,749 B2
(45) Date of Patent: Jul. 2, 2019

(54) METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE AND THE PURIFICATION THEREOF FOR USE AS AN ACTIVE PHARMACEUTICAL INGREDIENT

(71) Applicant: BAYER PHARMA AKTIENGESELLSCHAFT, Berlin (DE)

(72) Inventor: Johannes Platzek, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/753,849

(22) PCT Filed: Aug. 18, 2016

(86) PCT No.: PCT/EP2016/069558

§ 371 (c)(1),
(2) Date: Feb. 20, 2018

(87) PCT Pub. No.: WO2017/032673

PCT Pub. Date: Mar. 2, 2017

(65) Prior Publication Data

US 2018/0244670 A1 Aug. 30, 2018

(30) Foreign Application Priority Data

Aug. 21, 2015 (EP) .................................... 15182043

(51) Int. Cl.
*C07D 471/04* (2006.01)

(52) U.S. Cl.
CPC ........ *C07D 471/04* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 6,743,798 | B1 | 6/2004 | Straub et al. |
| 6,833,364 | B1 | 12/2004 | Straub et al. |
| 6,864,287 | B1 | 3/2005 | Alonso-Alija et al. |
| 7,087,644 | B1 | 8/2006 | Alonso-Alija et al. |
| 2002/0173514 | A1 | 11/2002 | Stasch et al. |
| 2004/0082798 | A1 | 4/2004 | Alonso-Alija et al. |
| 2004/0176446 | A1 | 9/2004 | Alonso-Alija et al. |
| 2006/0052397 | A1 | 3/2006 | Alonso-Alija et al. |
| 2008/0058314 | A1 | 3/2008 | Alonso-Alija et al. |
| 2010/0136142 | A1 | 6/2010 | Bärfacker et al. |
| 2017/0217957 | A1 | 8/2017 | Platzek et al. |

FOREIGN PATENT DOCUMENTS

| | | | |
|---|---|---|---|
| WO | 00/06568 | A1 | 2/2000 |
| WO | 00/06569 | A1 | 2/2000 |
| WO | 01/19355 | A2 | 3/2001 |
| WO | 01/19776 | A2 | 3/2001 |
| WO | 01/19778 | A1 | 3/2001 |
| WO | 01/19780 | A2 | 3/2001 |
| WO | 02/42301 | A1 | 5/2002 |
| WO | 02/070462 | A1 | 9/2002 |
| WO | 02/070510 | A2 | 9/2002 |
| WO | 03/095451 | A1 | 11/2003 |
| WO | 2008/104306 | A2 | 9/2008 |
| WO | 2016/016287 | A1 | 2/2016 |

OTHER PUBLICATIONS

Abe et al., "Large Scale Synthesis of N-benzyl-4-formylpiperidine through Partial Reduction of Esters using Aluminum Hydride Reagents Modified with Pyrrolidine," Tetrahedron, (Apr. 2, 2001), vol. 57, Issue 14, pp. 2701-2710.
Bärfacker et al., "Discovery of BAY 94/8862: A Nonsteroidal Antagonist of the Mineralocorticoid Receptor for the Treatment of Cardiorenal Diseases," ChemMedChem, (Aug. 2012), vol. 7, Issue 8, pp. 1385-1403.
Chang et al., "Highly Efficient Triarylene Conjugated Dyes for Sensitized Solar Cells," Journal of Materials Chemistry, (Jun. 2011), vol. 21, Issue 26, pp. 9523-9531.
Chidambaram, "A Robust Palladium-Catalyzed Cyanation Procedure: Beneficial Effect of Zinc Acetate," Tetrahedron Letters, (Feb. 9, 2004), vol. 45, Issue 7, pp. 1441-1444.
Garcia et al., "Chemoenzymatic Aminolysis and Ammonolysis of β-Ketoesters," Tetrahedron Letters, (Sep. 17, 1993), vol. 34, Issue 38, pp. 6141-6142.
Glennon et al., "Binding of Phenylalkylamine Derivatives at 5-HT1C and 5-HT2 Serotonin Receptors: Evidence for a Lack of Selectivity," Journal of Medicinal Chemistry, (Feb. 1992), vol. 35, No. 4, pp. 734-740.

(Continued)

*Primary Examiner* — Heidi Reese
(74) *Attorney, Agent, or Firm* — Ice Miller LLP

(57) ABSTRACT

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)

(I)

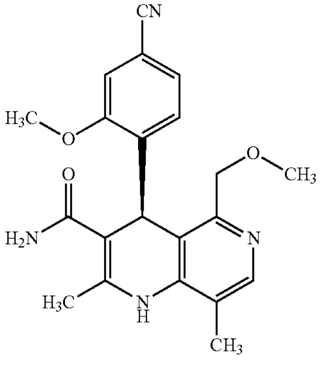

13 Claims, No Drawings

(56) References Cited

OTHER PUBLICATIONS

Grimster et al., "Aromatic Sulfonyl Fluorides Covalently Kinetically Stabilize Transthyretin to Prevent Amyloidogenesis while Affording a Fluorescent Conjugate," Journal of the American Chemical Society, (Jan. 25, 2013), vol. 135, No. 15, pp. 5656-5668.
Hagiya et al., "A Facile and Selective Synthetic Method for the Preparation of Aromatic Dialdehydes from Diesters via the Amine-Modified SMEAH Reduction System," Synthesis, (May 2003), Issue 6, pp. 823-828.
Hung et al., "A General Route to 5- and 6-Substituted 4-Amino-2-oxo-1,2-dihydropyridines," Synthesis, (1984), Issue 9, pp. 765-766.
Martin et al., "Open air Palladium Catalyzed Cyanation—the use of PMHS to Protect from Oxygen," Tetrahedron Letters, (Apr. 2, 2007), vol. 48, Issue 14, pp. 2555-2557.
Ogura et al., "Total Synthesis of Acerogenins E, G and K, and Centrolobol," Tetrahedron, (Apr. 1, 2013), vol. 69, Issue 13, pp. 2807-2815.
Patrick et al., "Synthesis and in Vitro Antiprotozoal Activities of Dicationic 3,5-Diphenylisoxazoles," Journal of Medicinal Chemistry, (Apr. 18, 2007), vol. 50, No. 10, pp. 2468-2485.
Schareina et al., "Improving Palladium-Catalyzed Cyanation of Arylhalides: Development of a state-of-the-art Methodology using Potassium Hexacyanoferrate(II) as Cyanating Agent," Journal of Organometallic Chemistry, (Nov. 29, 2004), vol. 689, Issue 24, pp. 4576-4583.
Schareina et al., "A new Palladium Catalyst System for the Cyanation of Aryl Chlorides with K4[Fe(CN)6]," Tetrahedron Letters, (Feb. 12, 2007), vol. 48, Issue 7, pp. 1087-1090.
Subramani et al., "Optimization of Reactive SMB and Varicol Systems," Computers and Chemical Engineering, (Dec. 15, 2003), vol. 27, Issue 12, pp. 1883-1901.
Sundermeier et al., "Ein praktikables Verfahren zur Palladiumkatalysierten Cyanierung von Arylhalogeniden," Angewandte Chemie, (Apr. 11, 2003), vol. 115, Issue 14, pp. 1700-1703.
Tromelin et al., "Synthese et etude biologique preliminaire de derives dichlorethylamines sur L'homocycle de nitro-2 benzofurannes," Eur. J. Med. Chem.—Chim. Ther., (1986), vol. 21, No. 5, pp. 397-402.
Tschaen et al., "An Improved Procedure for Aromatic Cyanation," Synthetic Communications, (1994), vol. 24, No. 6, pp. 887-890.
Zanon et al., "Copper-Catalyzed Domino Halide Exchange-Cyanation of Aryl Bromides," Journal of the American Chemical Society, (Feb. 15, 2003), vol. 125, No. 10, pp. 2890-2891.

METHOD FOR THE PREPARATION OF (4S)-4-(4-CYANO-2-METHOXYPHENYL)-5-ETHOXY-2,8-DIMETHYL-1,4-DIHYDRO-1-6-NAPHTHYRIDINE-3-CARBOXAMIDE AND THE PURIFICATION THEREOF FOR USE AS AN ACTIVE PHARMACEUTICAL INGREDIENT

The present invention relates to a novel and improved process for preparing (4S)-4-(4-cyano-2-methoxyphenyl)-5-ethoxy-2,8-dimethyl-1,4-dihydro-1,6-naphthyridine-3-carboxamide of the formula (I)

(I)

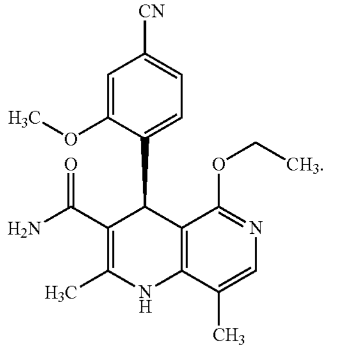

The compound of the formula (I) acts as a non-steroidal antagonist of the mineralocorticoid receptor and may be used as an agent for prophylaxis and/or treatment of cardiovascular and renal disorders such as heart failure and diabetic nephropathy, for example.

The compound of the formula (I) and the preparation process thereof are described in WO2008/104306 and ChemMedChem 2012, 7, 1385, both publications disclosing a detailed discussion of the research synthesis. A disadvantage of the synthesis described therein is the fact that this synthesis is unsuitable for a further large-scale process, since many steps proceed at very high dilution, with very high excesses of reagents and therefore afford a relatively low overall yield. Furthermore, many intermediate chromatographic purifications are necessary, which are technically generally very laborious and entail a high consumption of solvents, are costly and are therefore to be avoided if possible. Some stages are not achievable in an industrial scale process due to safety and process technology difficulties.

There existed a need, therefore, for an industrially practicable synthesis, which affords the compound of the formula (I) in a reproducible manner in high overall yield, low production costs and high purity and meets all regulatory requirements, in order to provide clinical trials with active ingredient and to be used for later regulatory submission.

In terms of the present invention, a very efficient synthesis has been found which allows the requirements mentioned above to be met.

In the publication ChemMedChem 2012, 7, 1385, which discloses the research scale synthesis of the compound of the formula (I), the compound of the formula (I) is prepared in 10 stages starting from vanillin with an overall yield of 3.76% of theory. The compound of the formula (I) was obtained by evaporation of chromatographic fractions as a solid; a defined crystallization process for the final stage for polymorphic adjustment has not been described to date.

The following scheme 1 shows the known process for preparing the compound of the formula (I).

Scheme 1: Research scale synthesis of the compound of the formula (I)

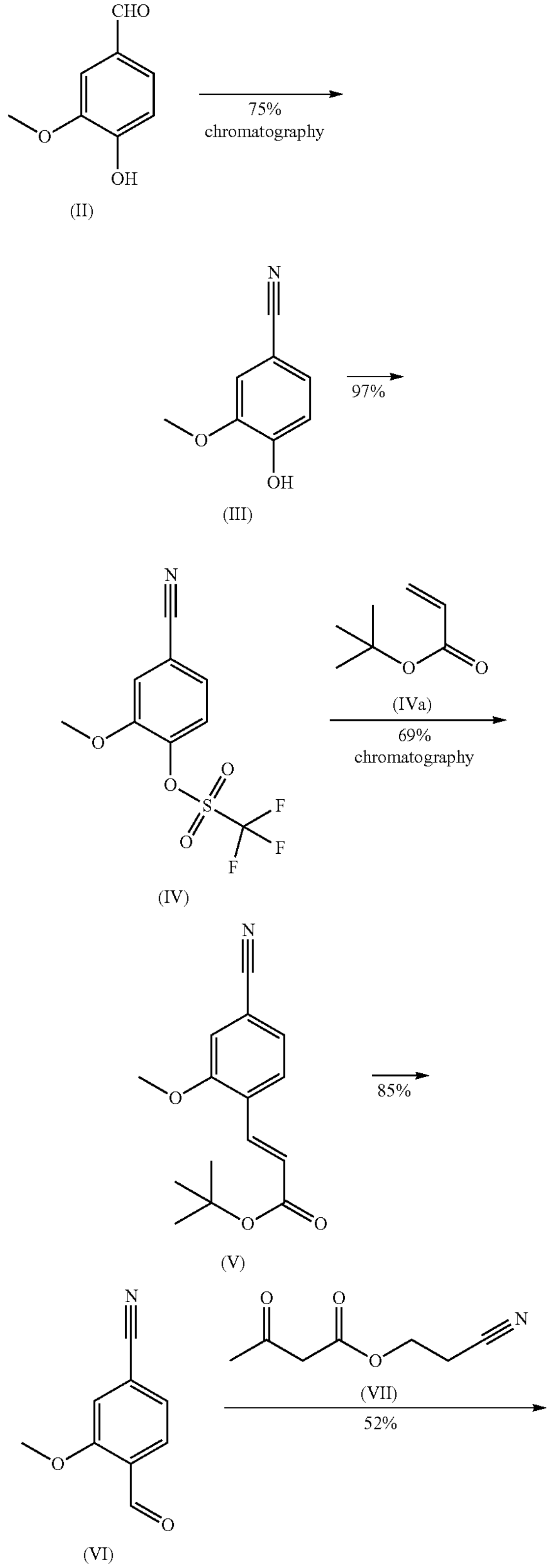

(II) (III) (IV) (IVa) (V) (VI) (VII)

-continued

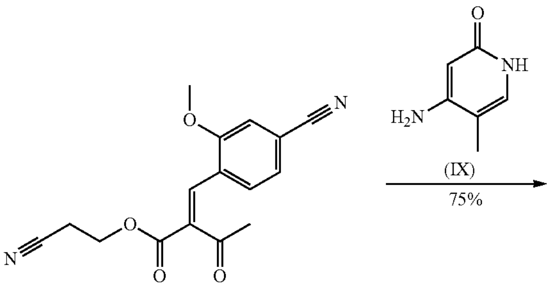

(VIII)

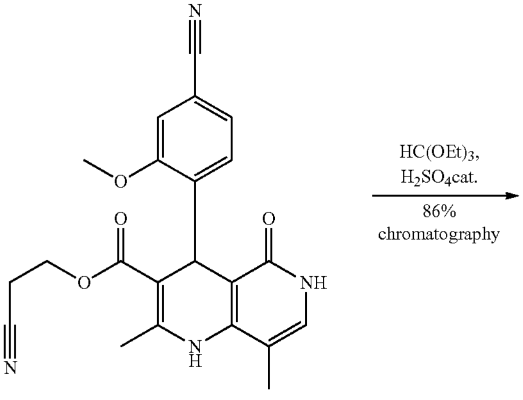

(X)

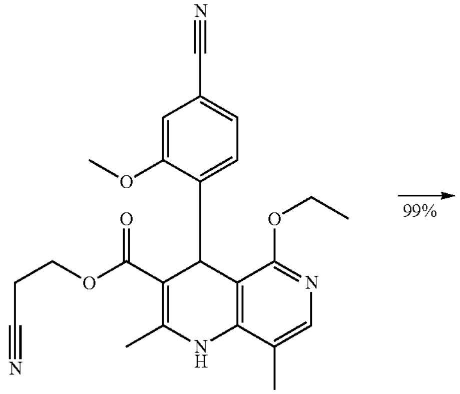

(XI)

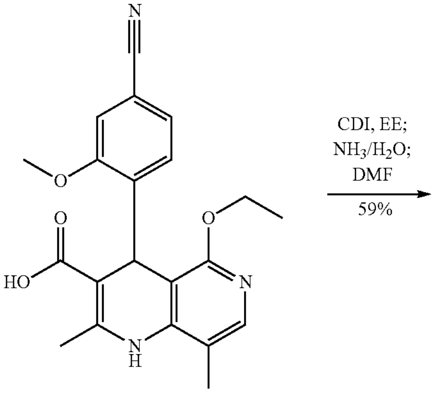

(XII)

-continued

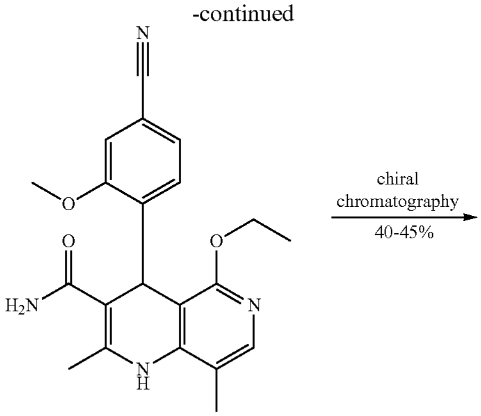

(XIII)

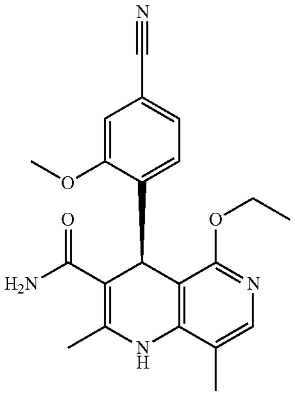

(I)

Three chromatographic purifications are utilized and also a chiral chromatography stage for separating the enantiomers of the racemate of the formula (XIII). Some of the stages proceed at very high dilution and using very large amounts of reagent.

For instance, the sequence of the preparation of the nitrile-aldehyde intermediate (VI) in particular, which takes on a central role in this synthesis, is also unacceptable in terms of atom economy.

Scheme 2 illustrates the novel process according to the invention, proceeding from nitrile aldehyde (VI), which affords the compound of the formula (I) in 4 stages in an overall yield of 31.5% of theory (8.8% of the above research synthesis proceeding from the aldehyde (VI)) without chromatographic purification of intermediates.

Scheme 2: Process according to the invention for preparing the compound of the formula (I).

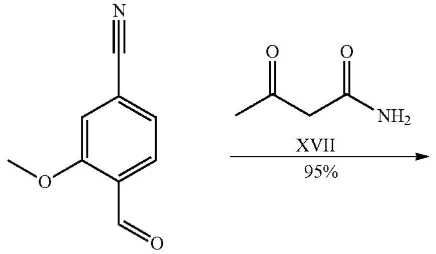

(VI)

-continued

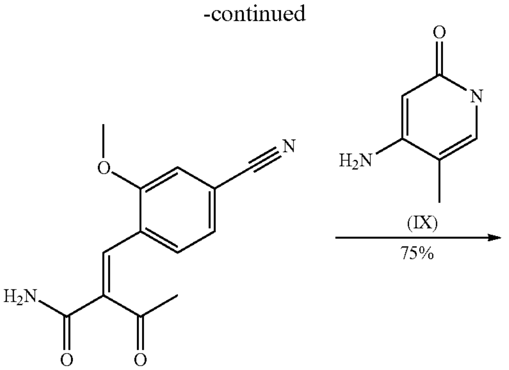

(XVI)

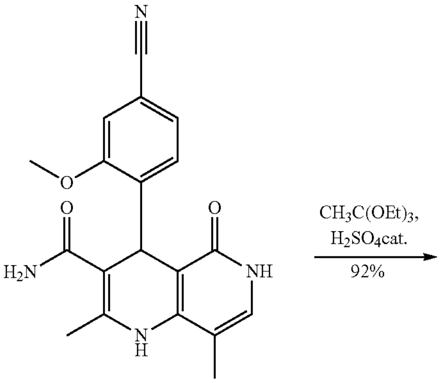

(XVIII)

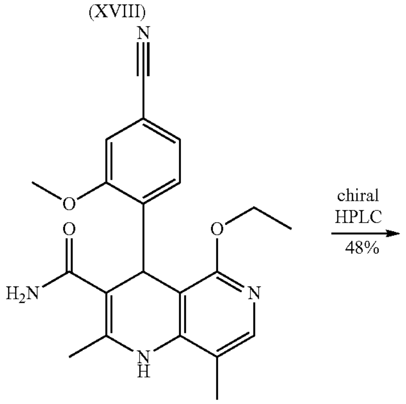

(XIII)

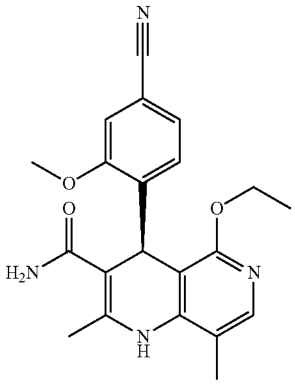

(I)

A preparative chiral HPLC method (e.g. SMB Technology, Varicol) is used for the enantiomer separation.

The aldehyde (VI) is known from the literature (J. Med. Chem. 2007, 50, 2468-2485) and constitutes an important intermediate in this synthesis. It is now also possible to purchase the compound commercially.

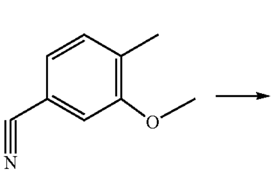

(VIa)

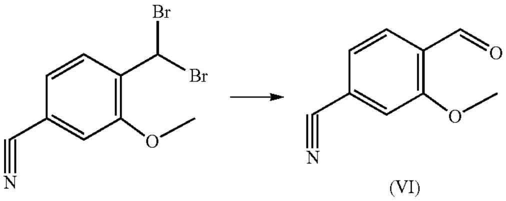

(VIb) (VI)

Starting from 4-cyano-2-methoxytoluene (VIa), a dibromide (VIb) is prepared with NBS, which is reacted in ethanol with 2.46 eq. of silver nitrate (in water) to give the target aldehyde (VI). This synthesis described in the literature and the process described in the research scale synthesis are completely unsuitable for scaling up to the multi-tonne scale such that a great need existed for a novel, more efficient and economically more viable synthesis.

The halobenzoic acids (XIV) and (XIVa)

(XIV)

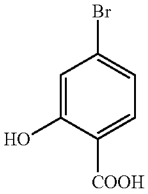

(XIVa)

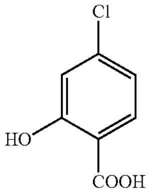

are commercially available in relatively large amounts. A very efficient and cheaper process has been developed in which the intermediates (XV) and (XIX)

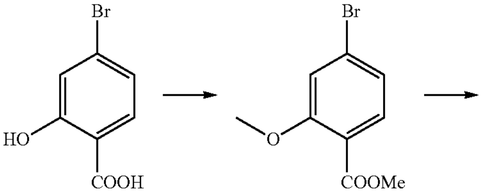

(XIV) (XV)

-continued

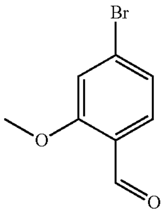

(XIX)

are not isolated but are further reacted dissolved in solution. This is only possible because the yield and purity of each reaction is very high (>95% of theory). The methyl ether ester (XV) is known from the literature (Journal of Medicinal Chemistry, 1992, vol. 35, p. 734-740) and is prepared by reaction with methyl iodide, which is very volatile, harmful to health and costly.

It was possible to show that the non-volatile, less expensive dimethyl sulphate can be used analogously. Starting from the acid (XIV), said acid is reacted in a solvent such as acetone, 2-butanone, THF, 2-methyl-THF, DMF, DMA or NMP with dimethyl sulphate with the aid of an auxiliary base such as potassium carbonate, sodium carbonate, calcium carbonate, lithium carbonate, N-methylimidazole, triethylamine, pyridine or 2,6-lutidine at temperatures of 50-100° C. to give the methyl ether ester (XV). This is a method known to those skilled in the art for esterification of acids and etherification of phenols (Tetrahedron, 2013, vol. 69, p. 2807-2815, Journal of the American Chemical Society, 2013, vol. 135, p. 5656-5668). The reaction in acetone under reflux (56° C.) using dimethyl sulphate and potassium carbonate has been found to be particularly preferred. In this case, dimethyl sulphate is added to the boiling reaction mixture over 4 hours. The acetone is distilled off and replaced by toluene (redistillation). For the work-up, water is added (decomposing the excess dimethyl sulphate), the toluene phase is separated and washed with water and saturated sodium chloride solution and the toluene solution subsequently distilled off to a certain volume (serves as azeotropic drying, i.e. removal of water for the subsequent stage). Determination of the solution content indicates virtually complete conversion (>96% of theory). Instead of the bromine compound, the chlorine compound may be used analogously for which the achieved conversions are identical to the bromine compound.

The preparation of the aldehyde (XIX) is described in the literature; the following are cited by way of example: Glaxo Group Limited US2008/312209 A1, 2008, European Journal of Medicinal Chemistry, 1986, vol. 21, p. 397-402, Journal of Medicinal Chemistry, 1992, vol. 35, p. 734-740, Journal of Materials Chemistry, 2011, vol. 21, p. 9523-9531. However, the starting materials used in the reactions are very expensive and not obtainable in large amounts, therefore a new method starting from the methyl ether ester (XV) was developed. The conversion of (XV) to the aldehyde (XIX) is possible using REDAL (sodium bis(2-methoxyethoxy)aluminium dihydride) in toluene by addition of N-methylpiperazine. This method is described in the literature (Synthesis 2003, No. 6, 823-828 and Tetrahedron 57 (2001) 2701-2710). If the reaction is carried out analogously to the stoichiometry stated in the literature, a further compound is found in the mixture in addition to the aldehyde. It was shown that this is the corresponding benzyl alcohol which is formed by overreduction of up to 10%. It was shown that it is important to adjust the stoichiometry of the REDAL and N-methylpiperazine to exactly 1.21 eq. of REDAL+1.28 eq. of N-methylpiperazine; in that case, it is possible to reduce the level of this by-product, which is disruptive in the subsequent crystallization stage, down to <1%. For this purpose, a 65% REDAL solution in toluene at 0-5° C. is charged (preferably 1.21 eq.) and 1.28 eq. of N-methylpiperazine are metered in. The solution of REDAL with N-methylpiperazine thus obtained is added over about 30 minutes to the bromo methyl ester solution (XIV) charged in toluene and the mixture is subsequently stirred for one hour at 0° C. The reaction solution is quenched in water/acid, preferably aqueous sulphuric acid and the toluene phase is separated and washed with water and saturated sodium chloride solution. The toluene is distilled off and redistilled in DMF (solvent for the subsequent stage). The reaction yield is generally >94% of theory. The corresponding reaction with the chloro compound proceeds analogously and the yields are equivalent. The DMF solution is used directly in the subsequent reaction.

Later on in the synthesis, the bromoaldehyde (XIX) is converted to the nitrile in a manner known per se by methods familiar to those skilled in the art (Synth. Commun. 1994, 887-890, Angew. Chemie 2003, 1700-1703, Tetrahedron Lett. 2007, 2555-2557, Tetrahedron Lett. 2004, 1441-1444, JACS 2003, 125, 2890-2891, Journal of Organometallic Chemistry 689 (2004), 4576-4583); this affords the nitrile aldehyde (VI). It has proven particularly advantageous in the case of the bromo compound to carry out a palladium-catalysed reaction with potassium hexacyanoferrate*3 $H_2O$ as the cyanide source (Tetrahedron Lett. 48 (2007), 1087-1090). For this purpose, the bromoaldehyde (XIX) is initially charged in DMF (8-10 times the amount), 0.22 eq. of potassium hexacyanoferrate*$3H_2O$ and 1 eq. of sodium carbonate are initially charged, and then 0.005 eq. of palladium acetate is added. The mixture is heated to 120° C. for 3 hours. The solution is cooled to 20° C., then water and ethyl acetate are added. The ethyl acetate phase is separated off, the water phase washed again with ethyl acetate and the combined ethyl acetate phases then redistilled in isopropanol. The product precipitates by water precipitation at the boiling temperature. After isolation, the product was dried under vacuum. In some cases, the product was precipitated directly from the DMF by addition of water and used directly in the subsequent stage after isolation and drying. The yields of this reaction are generally >85% of theory. Palladium acetate is inadequate for the conversion of the chlorine compound; it has been found here to be advantageous to use the palladium catalysts familiar to those skilled in the art, as described in Tetrahedron Lett. 48 (2007), 1087-1090; the yields are somewhat lower than in the case of the bromine compound, generally 80-85% of theory.

The cinnamide (XVI a,b) is obtained as an E/Z mixture starting from the aldehyde of the formula (VI) in a Knoevenagel reaction with the keto amide (XVII):

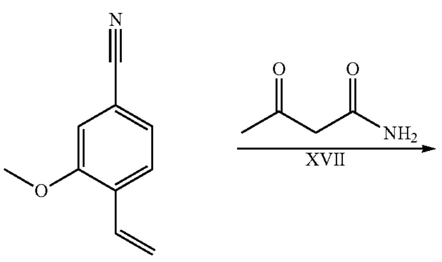

VI

-continued

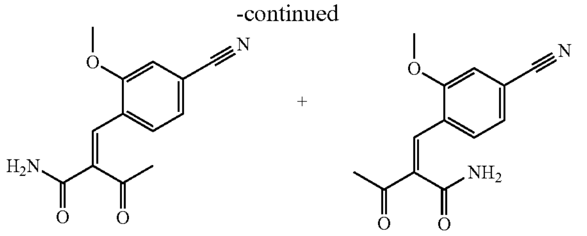

XVI a + b

The reaction proceeds preferably in boiling dichloromethane (10 to 20 times the amount) by addition of 5-20 mol % of piperidine, preferably 10 mol % and 5-20 mol % of glacial acetic acid, preferably 5-10 mol %, on a water separator. The reaction time is 4-12 h, but preferably 5-6 h, particularly preferably 6 h. The keto amide (XVII) is added in 1.0-1.5 eq, but preferably 1.1 to 1.35 eq. Particularly preferably 1.1 eq. The preparation of the keto amide (XVII) is known and described in Tetrahedron Letters, 1993, vol. 34, 6141-6142, but it is also commercially available. After completion, the reaction is cooled to 20° C. and the organic phase is washed twice with water. The organic wash is redistilled in 2-butanol and the E/Z cinnamide mixture (XVI a+b) is used directly without intermediate isolation in the subsequent reaction with the heterocycle (IX) to give the dihydropyridine (XVIII):

preferably 3-5 bar, 8-24 h) or in ethanol (90-130° C., 3-10 bar, 3-24 h), in 2-butanol (100° C.-130° C., 2-10 bar, preferably 3-5 bar, 8-24 h). For work-up, the mixture is cooled to 0° C. to 20° C., the crystals filtered off and washed with ethanol and then dried (in vacuum, 60° C.).

If the use of dichloromethane should be omitted for environmentally economic reasons, it has proven to be advantageous to prepare the cinnamide (XVI a,b) in isopropanol, in which case the aldehyde (VI) is charged in isopropanol (3-9 times the amount, preferably 5-7 times the amount) and 5-20 mol % of piperidine, preferably 5-10 mol %, and 5-20 mol % of glacial acetic acid, preferably 5-10 mol %, is added. At 30° C., 1.0-1.5 eq., preferably 1.1-1.35 eq., particularly preferably 1.1 eq., of keto amide (XVII), optionally dissolved in a little isopropanol, is metered in over the course of 3 hours and the mixture is stirred at 30° C. for 1 hour. The cinnamide (XVI a,b) crystallizes out during the reaction. The product is subsequently filtered off, optionally after cooling, preferably at 0° C., washed with a little isopropanol (cooled to 0° C.) and used moist in the subsequent reaction as described above. The yield is >95% of theory. The subsequent reaction is preferably performed in 10-15 times the amount (with respect to aldehyde (VI)), preferably 10-12 times the amount, of 2-butanol or isopropanol for 20-24 hours at 100° C. under pressure. After termination of the reaction and cooling, the product is isolated by filtration or centrifugation. The product is sub-

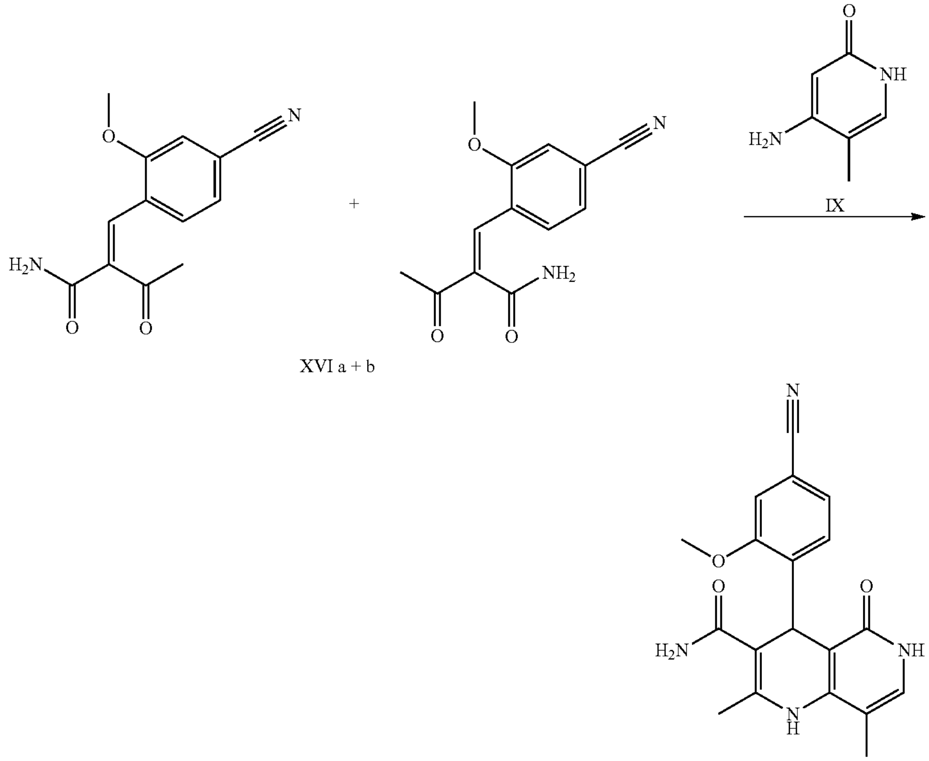

XVI a + b

XVIII

It has been found that the reaction is preferably carried out in alcohols such as ethanol, isopropanol, isobutanol (2-butanol), 2-amyl alcohol or cyclohexanol at temperatures of 80-160° C., at atmospheric pressure and also in autoclaves (2-10 bar), with reaction times of 8-40 h, but preferably in isopropanol in an autoclave (100° C.-130° C., 2-10 bar, sequently dried at 40-90° C. under vacuum. Since the conversion to the cinnamide (XVI a,b) proceeds virtually quantitatively, the process for the subsequent stage can be readily standardized without having to adjust the amount of heterocycle (IX) in each case, as the product can be used moist with isopropanol. The yields are >75% of theory. The heterocycle (IX) can be prepared by known literature methods such as is described, for example, in Synthesis 1984, 765-766.

Starting from the dihydropyridine (XVIII), the ethyl ether (XIII) is obtained by reaction under acidic catalysis with an orthoester (XX), where R is —H or -methyl:

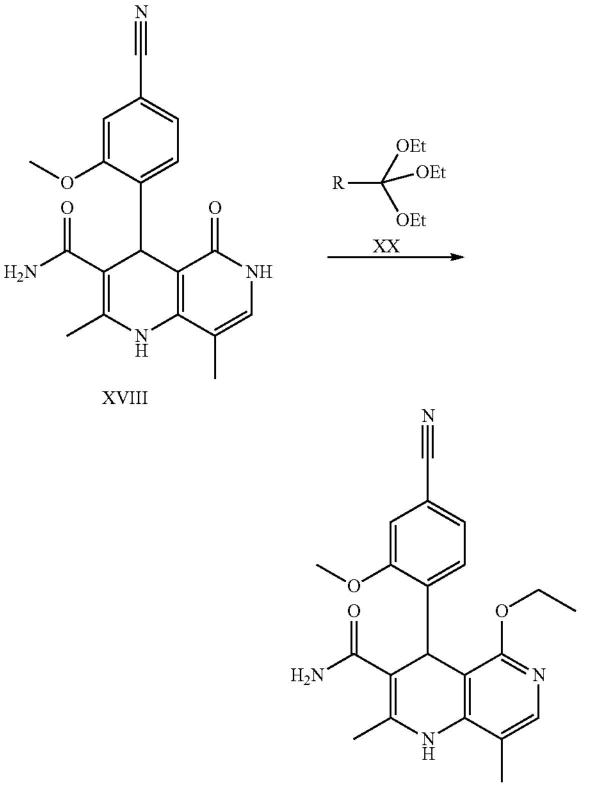

XVIII

XX

XIII

It has been found, surprisingly, that the reaction can be carried out in a very concentrated manner (up to 1.5 g of solvent per 1 g of reactant) in solvents such as dimethylacetamide, NMP (1-methyl-2-pyrrolidone) or DMF (dimethylformamide) by addition of 4-10% by weight, preferably 6-8% by weight, of conc. sulphuric acid. The reaction then surprisingly proceeds with only 2.5-5 eq. of orthoester (XX) (R═H or Me). It has been found that it is much more convenient to use the corresponding triethyl orthoacetate in the reaction, since it reacts much more cleanly on the one hand and is much less inflammable, making it particularly appropriate for the technical procedure. The reaction is preferably carried out in DMA (dimethylacetamide) and NMP (1-methyl-2-pyrrolidone), at temperatures of 100-120° C., preferably 115° C. Before starting the actual reaction, it has proven advantageous to distill off some of the solvent (DMD or NMP) at elevated temperature (100-120° C. under vacuum) in order to remove any residues of isopropanol present from the precursor, as otherwise undesirable by-products occur. The reaction mixture was then stirred for another 1.5-3 hours, preferably 2 hours. For the work-up, water is added directly to the mixture, wherein the product crystallizes out. In order to have a particularly stable and reproducible process, a portion of the water (e.g. ⅓) is first added, then seed crystals are added, and the remaining amount of the water is added. This procedure guarantees that the same crystal polymorph is always obtained, which shows the optimum isolation characteristics. The product is washed with water and dried. The yields are >92% of theory. The purity is generally >99% (HPLC, 100% method).

To obtain the compound of the formula (I), the racemic mixture of amides (XIII) must be separated into the antipodes. In the published research scale synthesis, a specifically synthesized chiral phase was used for this purpose (prepared in-house), which comprised N-(dicyclopropylmethyl)-$N^2$-methacryloyl-D-leucinamide as chiral selector. This selector was prepared in a multi-stage process and then polymerized on special silica gel. Methanol/ethyl acetate served as eluent. A major disadvantage of this method was the very low loading, 30 mg per separation on a 500*63 mm chromatography column, such that there was a high need to find as effective a separation method as possible which allows separation of antipodes to be performed in the multi-tonne range. It has been found, surprisingly, that the separation can also be performed on a readily commercially available phase. This takes the form of the phase Chiralpak AS-V, 20 µm. The eluent used was a mixture of methanol/acetonitrile 60:40. This mixture has the major advantage that it can be recovered as eluent after distillative work-up having the identical composition (60:40, corresponds to the azeotrope). A very efficient process is achieved in this way in which the yield of the separation is >47% of theory (50% is theoretically possible). The optical purity here is >93% e.e. but preferably >98.5% e.e. In this case, the chromatography may be carried out on a conventional chromatography column, but preferably the techniques known to those skilled in the art such as SMB or Varicol (Computers and Chemical Engineering 27 (2003) 1883-1901) are used. For instance, about 500 kg of the racemic amide (XIII) was separated using an SMB system, in which a yield of 48% was achieved. The product is obtained as a 3-8%, preferably 5-7% solution in a mixture of methanol/acetonitrile 60:40 and can be used directly in "final processing". Other solvent mixture ratios of acetonitrile to methanol are also conceivable (90:10 to 10:90). Alternatively, other solvent mixtures can also be used, however, for the SMB separation, such as acetonitrile/ethanol in mixture ratios of 10:90 to 90:10. The particular solvent ratio depends partly on the technical properties of the SMB system and must be adjusted, if appropriate (e.g. varying flow rate, recycling of the solvent on a thin film evaporator).

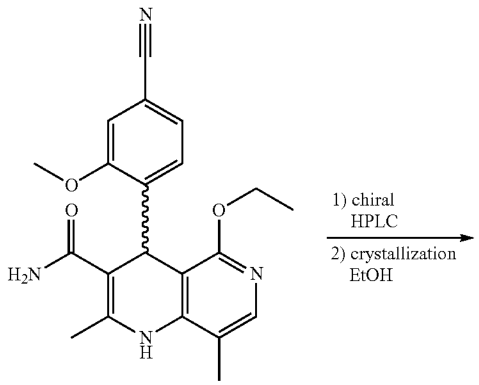

(XIII)

-continued

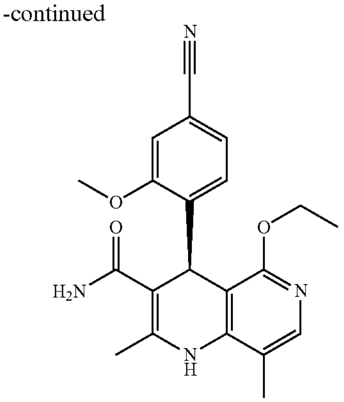

(I)

Since the compound of the formula (I) has been developed in the form of a tablet, there is a great need for isolation of an isolated compound of the formula (I) in a reproducible manner in a defined crystalline form which ensures reproducible bioavailability. It has been found, surprisingly, that the compound of the formula (I) can be crystallized from methanol, ethanol, THF, acetonitrile, and also mixtures thereof with water, wherein only one polymorph I is reproducibly formed, which has a defined melting point of 252° C. By way of advantage, ethanol or denatured ethanol is used.

Final crystallization process: For this purpose, the about 5-7% product solution in methanol/acetonitrile 60:40 (or, if ethanol/acetonitrile was employed, an about 3-4% solution of ethanol/acetonitrile 50:50) originating from the chromatography is firstly subjected to a particle filtration for GMP technical reasons and subsequently a solvent exchange with ethanol is performed, preferably using ethanol denatured with toluene. For this purpose, the solution is repeatedly redistilled, concentrated and fresh ethanol added each time. After exchange, as much ethanol is added until a solution phase is passed through at the boiling point and then it is concentrated under atmospheric pressure or under slightly reduced pressure to about 3 to 4 times the volume, in the course of which the product crystallizes out. This is cooled to 0° C. and the crystals then isolated and dried at 40-50° C. under vacuum. The yields are generally >90% of theory. The chemical purity achieved is >99.8% and the content ~100% correspond to the criteria for commercial products according to ICH guidelines. Residual solvent, in the case of ethanol, is <0.02%. The optical purity is >>99% e.e.

After crystallization, the compound of the formula (I) is in the crystalline form of polymorph I (I)

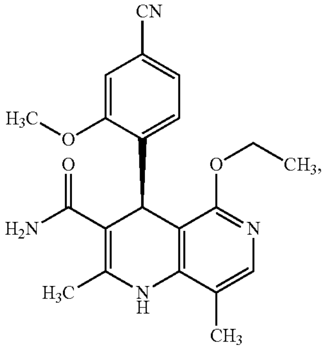

characterized in that the x-ray diffractogram of the compound exhibits peak maxima of the 2 theta angle at 8.5, 14.1, 17.2, 19.0, 20.5, 25.6, 26.5.

The compound of the formula (I) is in the crystalline form of polymorph I (I)

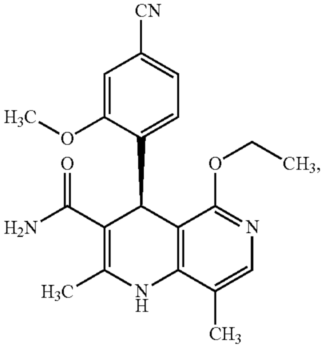

characterized in that the IR spectrum (IR-ATR) of the compound exhibits band maxima at 3475, 2230, 1681, 1658, 1606, 1572, 1485, 1255, 1136 and 1031 $cm^{-1}$.

The compound of the formula (I) is in the crystalline form of polymorph I (I)

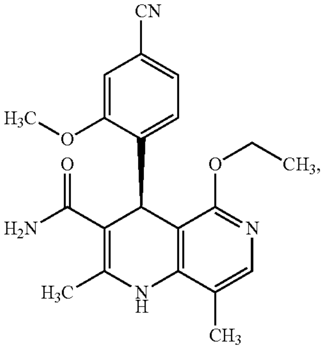

characterized in that the Raman spectrum of the compound exhibits band maxima at 3074, 2920, 2231, 1601, 1577, 1443, 1327, 1267, 827 and 155 $cm^{-1}$.

The compound of the formula (I) is generally micronized and formulated pharmaceutically to tablets. It is found that the compound of the formula (I) in crystalline form of polymorph I has very good stability properties (even at high atmospheric humidity) and can be stored without any problem for >2 years.

With the synthesis according to the invention, it is possible to prepare the compound of the formula (I) in a very efficient manner. The process offers considerable advantages compared to the prior art relating to scalability and technical performance. The overall yield is significantly higher compared to published data and excellent purities of the active ingredient are also achieved. The novel process enables the reproducible, economic preparation of the defined compound of the formula (I) in crystalline form of polymorph I, of which the existence in the prior art has nowhere been described.

The present invention provides a process for preparing the compound of the formula (I)

(I)

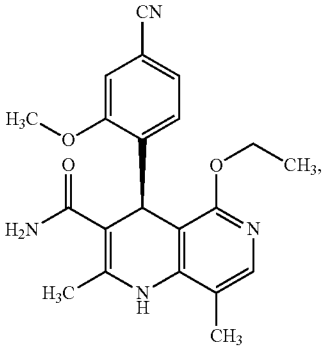

characterized in that the racemic compound of the formula (XIII) is separated into its enantiomers, and the compound of the formula (XIII)

XIII

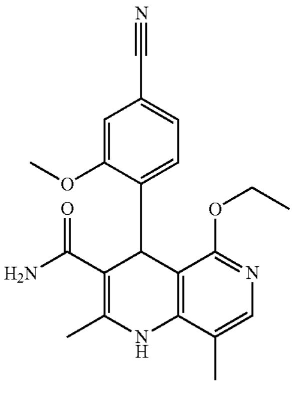

is prepared by reacting the compound of the formula (XVIII)

XVIII

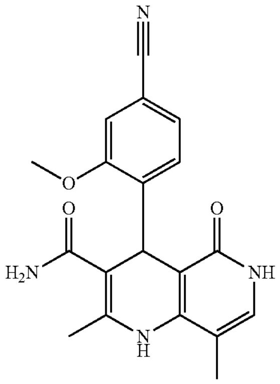

with the orthoester (XX)

(XX)

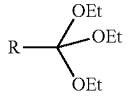

where R may be H or methyl, and
the compound of the formula (XVIII)

(XVIII)

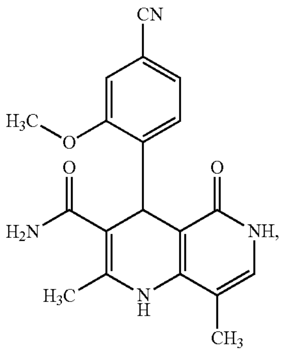

is prepared by reacting the compounds of the formula (XVI a,b)

XVI a+b

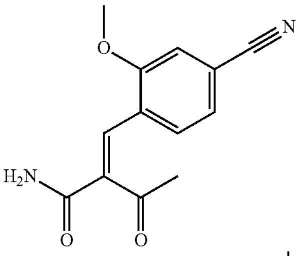

+

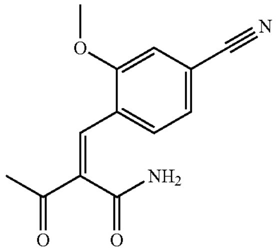

with the compound of the formula (IX)

IX

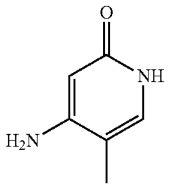

and
the compound of the formula (XVI a,b) is prepared by reacting the compound of the formula (VI)

VI

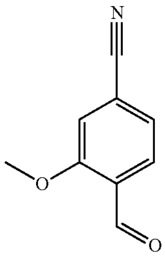

with the compound of the formula (XVII)

(XVII)

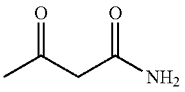

The present invention further provides a process for preparing the compound of the formula (I)

(I)

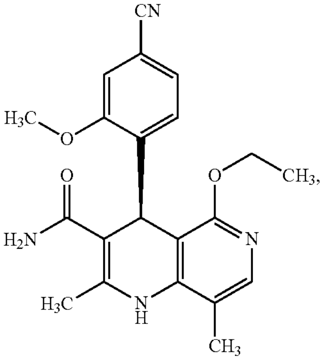

characterized in that the racemic compound of the formula (XIII) is separated into its enantiomers, where the compound of the formula (XIII)

XIII

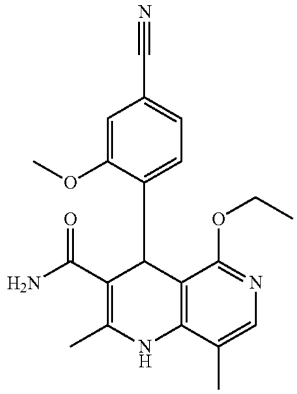

is prepared by reacting the compound of the formula (XVIII)

XVIII

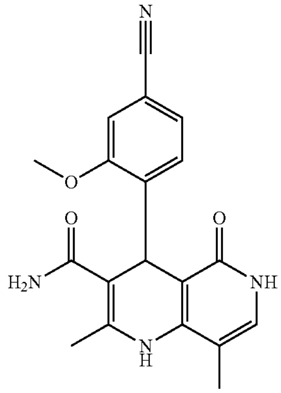

with the orthoester (XX)

(XX)

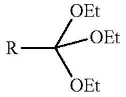

where R may be H or methyl, and the compound of the formula (XVIII)

(XVIII)

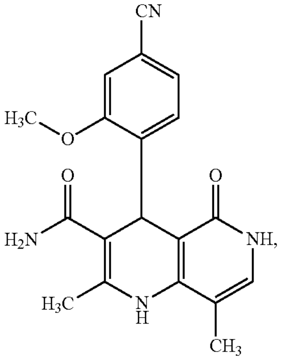

is prepared by reacting the compounds of the formula (XVI a,b)

XVI a+b

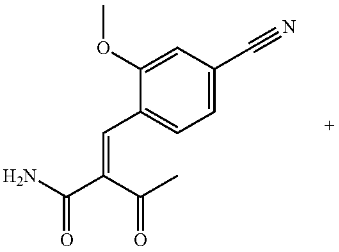

-continued

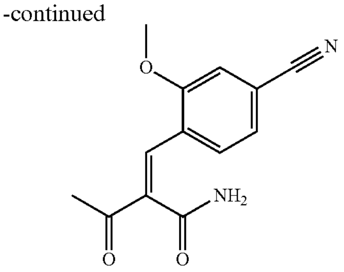

with the compound of the formula (IX)

IX

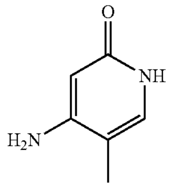

The present invention further provides a process for preparing the compound of the formula (I)

(I)

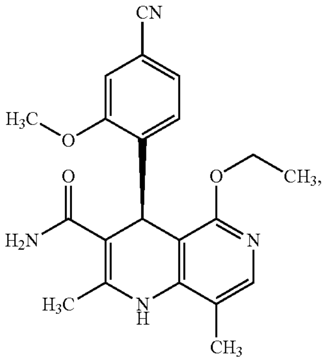

characterized in that the racemic compound of the formula (XIII) is separated into its enantiomers, where the compound of the formula (XIII)

XIII

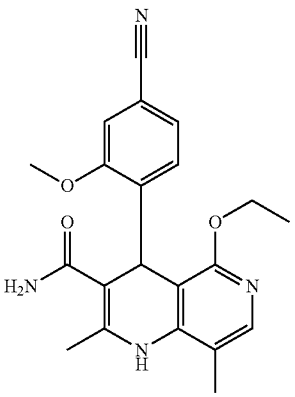

is prepared by reacting the compound of the formula (XVIII)

XVIII

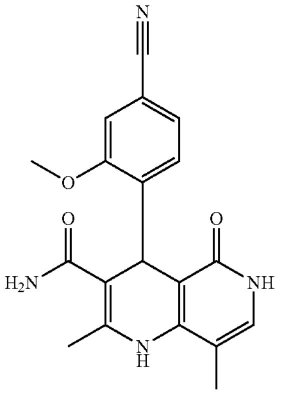

with the orthoester (XX)

(XX)

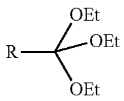

where R may be H or methyl.

The present invention further provides a process for preparing the compound of the formula (I)

(I)

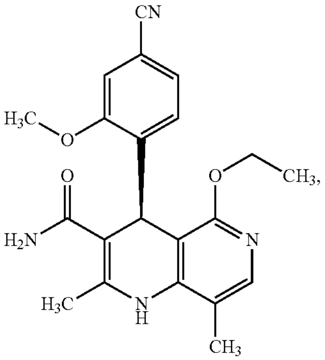

using the compound of the formula (XVIII)

(XVIII)

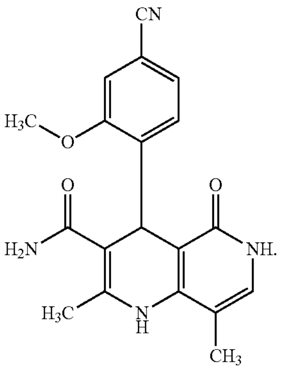

The present invention further provides a process for preparing the compound of the formula (I)

(I)

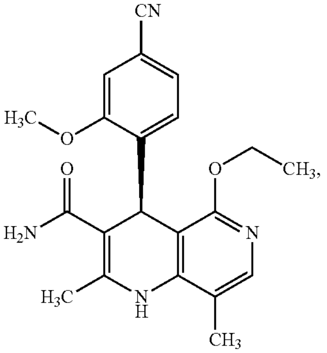

using the compounds of the formula (XVI a,b)

XVI a+b

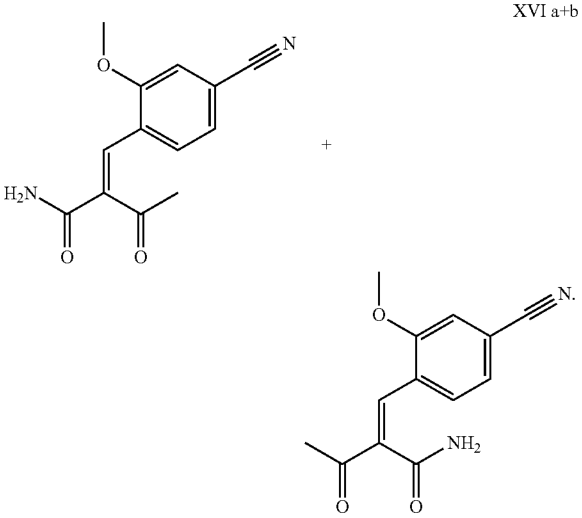

The present invention further provides a process for preparing the compound of the formula (I)

(I)

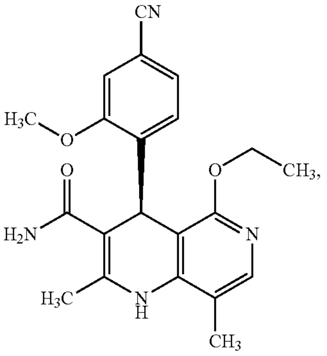

using the compound of the formula (XVIII)

(XVIII)

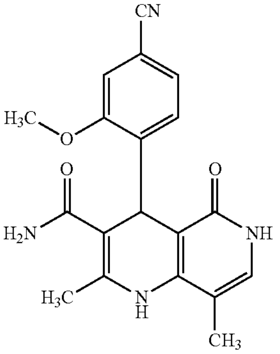

and the compounds of the formula (XVI a,b)

XVI a+b

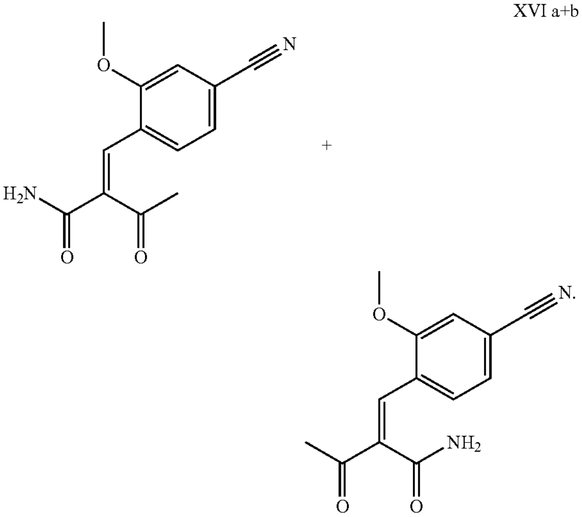

The present invention further provides a compound of the formula (XVIII)

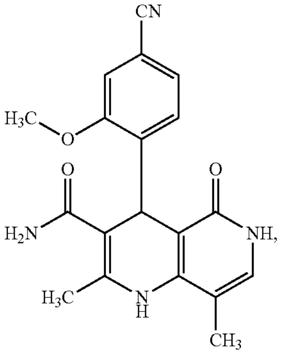

and the salts, solvates and solvates of the salts thereof.

The present invention further provides a compound of the formula as an E/Z mixture XVI a+b

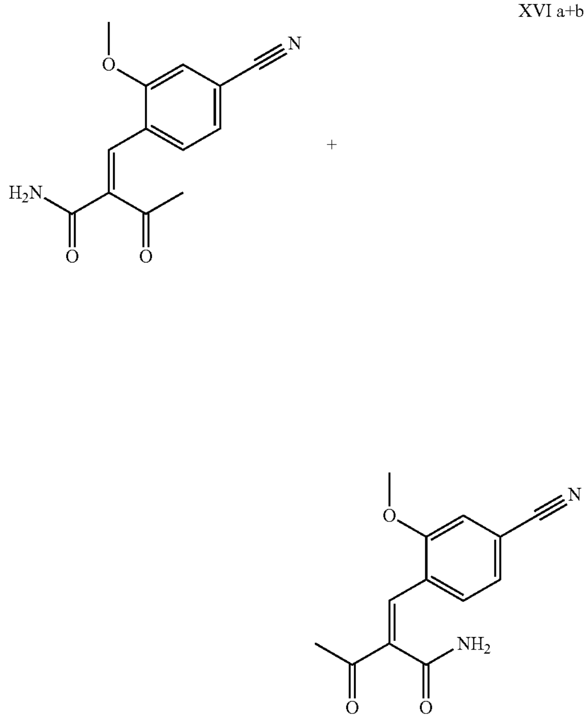

and the salts, solvates and solvates of the salts thereof.

The present invention further provides a process for preparing the compound of the formula (XVIII)

(XVIII)

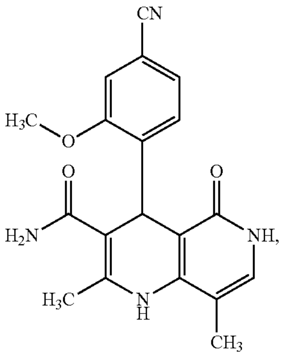

characterized in that the compounds of the formula (XVI a,b)

XVI a+b

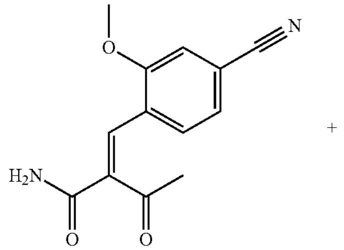

-continued

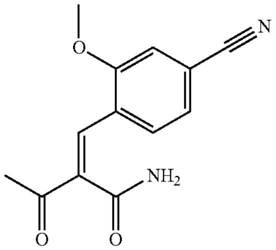

are reacted with the compound of the formula (IX)

IX

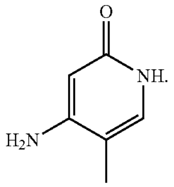

The present invention further provides a process for preparing the compounds of the formula (XVI a,b)

XVI a+b

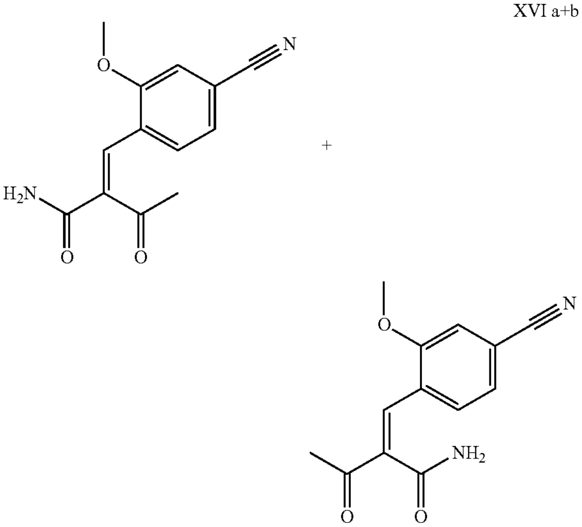

characterized in that the compound of the formula (VI)

VI

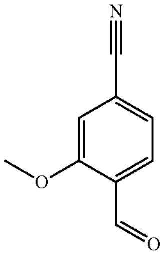

is reacted with the compound of the formula (XVII)

(XVII)

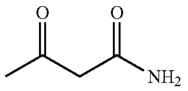

The present invention further provides a process for preparing the compound (XIII)

XIII

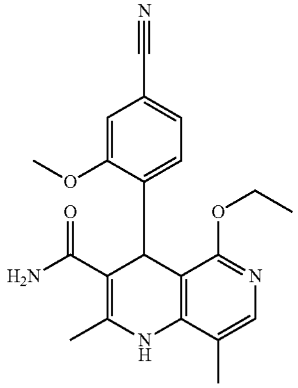

characterized in that the compound of the formula (XVIII)

(XVIII)

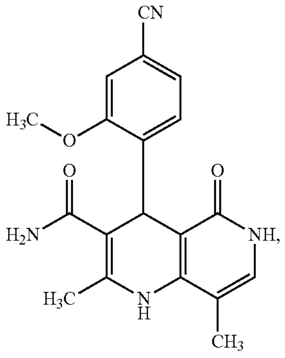

is reacted with the orthoester (XX)

(XX)

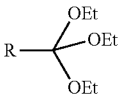

where R may be H or methyl.

The present invention further provides a process for preparing the compound of the formula (XIII)

XIII

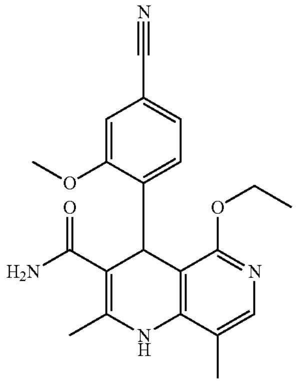

characterized in that the compound of the formula (XVIII)

(XVIII)

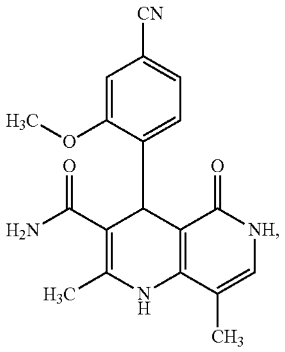

is reacted with the orthoester (XX)

(XX)

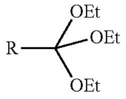

where R may be H or methyl, and characterized in that the compound of the formula (XVIII) is prepared by reacting the compounds of the formula (XVI a,b)

XVI a+b

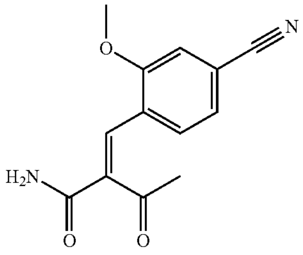

+

-continued

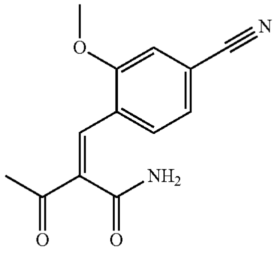

with the compound of the formula (IX)

IX

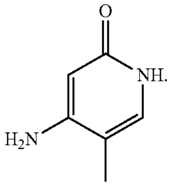

A further subject disclosed is a process for preparing the compound of the formula (I) in crystalline polymorph I (I)

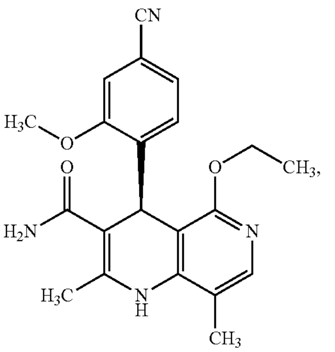

according to the above-described processes for preparing the compound of the formula (I), characterized in that the compound of the formula (I), present in one or more polymorphs or as a solvate in an inert solvent, is stirred at a temperature of 20° C.-120° C. and the compound of the formula (I) is isolated in crystalline polymorph I.

The compounds according to the invention, the compound of the formula (I) and the compound of the formula (I) in crystalline form of polymorph I (referred to hereinafter as compounds according to the invention) act as antagonists of the mineralocorticoid receptor and exhibit an unforeseeable, useful spectrum of pharmacological activity. They are therefore suitable for use as medicaments for treatment and/or prophylaxis of diseases in humans and animals.

The compounds according to the invention are suitable for the prophylaxis and/or treatment of various disorders and disease-related conditions, especially of disorders characterized either by an increase in the aldosterone concentration in the plasma or by a change in the aldosterone plasma concentration relative to the renin plasma concentration, or associated with these changes. Examples include: idiopathic primary hyperaldosteronism, hyperaldosteronism associated with adrenal hyperplasia, adrenal adenomas and/or adrenal carcinomas, hyperaldosteronism associated with cirrhosis of the liver, hyperaldosteronism associated with heart failure, and (relative) hyperaldosteronism associated with essential hypertension.

The compounds according to the invention are also suitable, because of their mechanism of action, for the prophylaxis of sudden cardiac death in patients at increased risk of dying of sudden cardiac death. In particular, these are patients who suffer, for example, from any of the following disorders: primary and secondary hypertension, hypertensive heart disease with or without congestive heart failure, treatment-resistant hypertension, acute and chronic heart failure, coronary heart disease, stable and unstable angina pectoris, myocardial ischaemia, myocardial infarction, dilative cardiomyopathies, inherited primary cardiomyopathies, for example Brugada syndrome, cardiomyopathies caused by Chagas disease, shock, arteriosclerosis, atrial and ventricular arrhythmia, transient and ischaemic attacks, stroke, inflammatory cardiovascular disorders, peripheral and cardiac vascular disorders, peripheral blood flow disturbances, arterial occlusive disorders such as intermittent claudication, asymptomatic left-ventricular dysfunction, myocarditis, hypertrophic changes to the heart, pulmonary hypertension, spasms of the coronary arteries and peripheral arteries, thromboses, thromboembolic disorders, and vasculitis.

The compounds according to the invention can also be used for the prophylaxis and/or treatment of oedema formation, for example pulmonary oedema, renal oedema or heart failure-related oedema, and of restenoses such as following thrombolysis therapies, percutaneous transluminal angioplasties (PTA) and percutaneous transluminal coronary angioplasties (PTCA), heart transplants and bypass operations.

The compounds according to the invention are further suitable for use as a potassium-saving diuretic and for electrolyte disturbances, for example hypercalcaemia, hypernatraemia or hypokalaemia.

The compounds according to the invention are equally suitable for treatment of renal disorders, such as acute and chronic renal failure, hypertensive renal disease, arteriosclerotic nephritis (chronic and interstitial), nephrosclerosis, chronic renal insufficiency and cystic renal disorders, for prevention of renal damage which can be caused, for example, by immunosuppressives such as cyclosporin A in the case of organ transplants, and for renal cancer.

The compounds according to the invention can additionally be used for the prophylaxis and/or treatment of diabetes mellitus and diabetic sequelae, for example neuropathy and nephropathy.

The compounds according to the invention can also be used for the prophylaxis and/or treatment of microalbuminuria, for example caused by diabetes mellitus or high blood pressure, and of proteinuria.

The compounds according to the invention are also suitable for the prophylaxis and/or treatment of disorders associated either with an increase in the plasma glucocorticoid concentration or with a local increase in the concentration of glucocorticoids in tissue (e.g. of the heart). Examples include: adrenal dysfunctions leading to overproduction of glucocorticoids (Cushing's syndrome), adrenocortical tumours with resulting overproduction of glucocorticoids, and pituitary tumours which autonomously produce ACTH (adrenocorticotropic hormone) and thus lead to adrenal hyperplasias with resulting Cushing's disease.

The compounds according to the invention can additionally be used for the prophylaxis and/or treatment of obesity, of metabolic syndrome and of obstructive sleep apnoea.

The compounds according to the invention can also be used for the prophylaxis and/or treatment of inflammatory disorders caused for example by viruses, spirochetes, fungi, bacteria or mycobacteria, and of inflammatory disorders of unknown etiology, such as polyarthritis, lupus erythematosus, peri- or polyarteritis, dermatomyositis, scleroderma and sarcoidosis.

The compounds according to the invention can further be employed for the treatment of central nervous disorders such as depression, states of anxiety and chronic pain, especially migraine, and for neurodegenerative disorders such as Alzheimer's disease and Parkinson's syndrome.

The compounds according to the invention are also suitable for the prophylaxis and/or treatment of vascular damage, for example following procedures such as percutaneous transluminal coronary angioplasty (PTCA), implantation of stents, coronary angioscopy, reocclusion or restenosis following bypass operations, and for endothelial dysfunction, for Raynaud's disease, for thromboangiitis obliterans (Buerger's syndrome) and for tinnitus syndrome.

Further disclosed by the present invention is the use of the compounds according to the invention for treatment and/or prevention of disorders, in particular the disorders mentioned above.

Further disclosed by the present invention is the use of the compounds according to the invention for producing a medicament for the treatment and/or prevention of disorders, especially of the aforementioned disorders.

Further disclosed by the present invention is a method of treatment and/or prevention of disorders, especially of the aforementioned disorders, using an effective amount of at least one of the compounds according to the invention.

The compounds according to the invention can be used alone or, if required, in combination with other active compounds. Further disclosed by the present invention are medicaments comprising at least one of the compounds according to the invention and one or more further active ingredients, in particular for the treatment and/or prevention of the disorders mentioned above. Preferred examples of active ingredients suitable for combinations include:

- active ingredients which lower blood pressure, for example and with preference from the group of calcium antagonists, angiotensin AII antagonists, ACE inhibitors, endothelin antagonists, renin inhibitors, alpha-receptor blockers, beta-receptor blockers and Rho kinase inhibitors;
- diuretics, especially loop diuretics, and thiazides and thiazide-like diuretics;
- antithrombotic agents, by way of example and with preference from the group of the platelet aggregation inhibitors, the anticoagulants or the profibrinolytic substances;
- active ingredients which alter lipid metabolism, for example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists;
- organic nitrates and NO donors, for example sodium nitroprusside, nitroglycerin, isosorbide mononitrate, isosorbide dinitrate, molsidomine or SIN-1, and inhaled NO;
- compounds having a positive inotropic effect, for example cardiac glycosides (digoxin), beta-adrenergic and dopaminergic agonists such as isoproterenol, adrenaline, noradrenaline, dopamine and dobutamine;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, and PDE 3 inhibitors such as amrinone and milrinone;
- natriuretic peptides, for example atrial natriuretic peptide (ANP, anaritide), B-type natriuretic peptide or brain natriuretic peptide (BNP, nesiritide), C-type natriuretic peptide (CNP) and urodilatin;
- calcium sensitizers, a preferred example being levosimendan;
- NO-independent but haem-dependent stimulators of guanylate cyclase, such as especially the compounds described in WO 00/06568, WO 00/06569, WO 02/42301 and WO 03/095451;
- NO- and haem-independent activators of guanylate cyclase, such as especially the compounds described in WO 01/19355, WO 01/19776, WO 01/19778, WO 01/19780, WO 02/070462 and WO 02/070510;
- inhibitors of human neutrophil elastase (HNE), for example sivelestat or DX-890 (Reltran);
- compounds which inhibit the signal transduction cascade, for example tyrosine kinase inhibitors, especially sorafenib, imatinib, gefitinib and erlotinib; and/or
- compounds which influence the energy metabolism of the heart, preferred examples being etomoxir, dichloroacetate, ranolazine or trimetazidine.

In a preferred embodiment, the compounds according to the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Agents which lower blood pressure are preferably understood to mean compounds from the group of calcium antagonists, angiotensin AII antagonists, ACE inhibitors, endothelin antagonists, renin inhibitors, alpha-receptor blockers, beta-receptor blockers, Rho kinase inhibitors, and the diuretics.

In a preferred embodiment, the compounds according to the invention are administered in combination with a calcium antagonist, by way of example and with preference nifedipine, amlodipine, verapamil or diltiazem.

In a preferred embodiment, the compounds according to the invention are administered in combination with an angiotensin AII antagonist, preferred examples being losartan, candesartan, valsartan, telmisartan or embusartan.

In a preferred embodiment, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment, the compounds according to the invention are administered in combination with an endothelin antagonist, by way of example and with preference bosentan, darusentan, ambrisentan or sitaxsentan.

In a preferred embodiment, the compounds according to the invention are administered in combination with a renin inhibitor, by way of example and with preference aliskiren, SPP-600, SPP-635, SPP-676, SPP-800 or SPP-1148.

In a preferred embodiment, the compounds according to the invention are administered in combination with an alpha-1-receptor blocker, by way of example and with preference prazosin.

In a preferred embodiment, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment, the compounds according to the invention are administered in combination with a rho kinase inhibitor, by way of example and with preference fasudil, Y-27632, SLx-2119, BF-66851, BF-66852, BF-66853, KI-23095 or BA-1049.

Antithrombotic agents (antithrombotics) are preferably understood to mean compounds from the group of platelet aggregation inhibitors, of anticoagulants or of profibrinolytic substances.

In a preferred embodiment, the compounds according to the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment, the compounds according to the invention are administered in combination with a GPIIb/IIIa antagonist, by way of example and with preference tirofiban or abciximab.

In a preferred embodiment, the compounds according to the invention are administered in combination with a factor Xa inhibitor, by way of example and with preference rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment, the compounds according to the invention are administered in combination with heparin or with a low molecular weight (LMW) heparin derivative.

In a preferred embodiment, the compounds according to the invention are administered in combination with a vitamin K antagonist, by way of example and with preference coumarin.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment, the compounds according to the invention are administered in combination with a CETP inhibitor, by way of example and with preference torcetrapib (CP-529 414), JJT-705, BAY 60-5521, BAY 78-7499 or CETP vaccine (Avant).

In a preferred embodiment, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment, the compounds according to the invention are administered in combination with an HMG-CoA reductase inhibitor from the class of statins, by way of example and with preference lovastatin, simvastatin, pravastatin, fluvastatin, atorvastatin, rosuvastatin, cerivastatin or pitavastatin.

In a preferred embodiment, the compounds according to the invention are administered in combination with a squalene synthesis inhibitor, by way of example and with preference BMS-188494 or TAK-475.

In a preferred embodiment, the compounds according to the invention are administered in combination with an ACAT inhibitor, by way of example and with preference avasimibe, melinamide, pactimibe, eflucimibe or SMP-797.

In a preferred embodiment, the compounds according to the invention are administered in combination with an MTP inhibitor, by way of example and with preference implitapide, BMS-201038, R-103757 or JTT-130.

In a preferred embodiment, the compounds according to the invention are administered in combination with a PPAR-gamma agonist, by way of example and with preference pioglitazone or rosigli alone.

In a preferred embodiment, the compounds according to the invention are administered in combination with a PPAR-delta agonist, by way of example and with preference GW-501516 or BAY 68-5042.

In a preferred embodiment, the compounds according to the invention are administered in combination with a cholesterol absorption inhibitor, by way of example and with preference ezetimibe, tiqueside or pamaqueside.

In a preferred embodiment, the compounds according to the invention are administered in combination with a lipase inhibitor, by way of example and with preference orlistat.

In a preferred embodiment, the compounds according to the invention are administered in combination with a polymeric bile acid adsorber, by way of example and with preference cholestyramine, colestipol, colesolvam, CholestaGel or colestimide.

In a preferred embodiment, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment, the compounds according to the invention are administered in combination with a lipoprotein(a) antagonist, by way of example and with preference gemcabene calcium (CI-1027) or nicotinic acid.

Further disclosed by the present invention are medicaments which comprise at least one compound according to the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral and intravenous administration.

The compounds according to the invention can be converted to the administration forms mentioned. This can be accomplished in a manner known per se by mixing with inert, non-toxic, pharmaceutically suitable auxiliaries. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of body weight, route of administration, individual response to the active compound, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

EXPERIMENTAL

Abbreviations and Acronyms

MS: mass from mass spectrometry

HPLC: high-performance liquid chromatography

DMF: dimethylformamide

Red-Al solution in toluene: sodium bis(2-methoxyethoxy) aluminium dihydride in toluene THF: tetrahydrofuran Aqu. HCl: aqueous hydrochloric acid DMAP: 4-(dimethylamino)pyridine

EXAMPLES

Example 1

Methyl 4-bromo-2-methoxybenzoate (XV)

(XV)

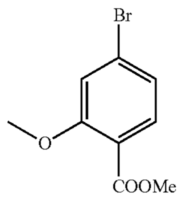

3.06 kg (22.12 mol) of potassium carbonate were initially charged in 3.6 l of acetone and heated to reflux. To this suspension were added 1.2 kg of 4-bromo-2-hydroxybenzoic acid (5.53 mol), suspended in 7.8 l of acetone, and were rinsed in with 0.6 l of acetone. The suspension was heated under reflux for 1 hour (vigorous evolution of gas!). 2.65 kg (21.01 mol) of dimethyl sulphate were then added over 4 hours while boiling. The mixture was subsequently stirred under reflux for 2.5 hours. The solvent was largely distilled off (to the point of stirrability) and 12 l of toluene were added and the residual acetone was then distilled off at 110° C. About 3 l of distillate were distilled off, this being supplemented by addition of a further 3 l of toluene to the mixture. The mixture was allowed to cool to 20° C. and 10.8 l of water were added and vigorously stirred in. The organic phase was separated off and the aqueous phase was extracted once more with 6.1 l of toluene. The combined organic phases were washed with 3 l of saturated sodium chloride solution and the toluene phase is concentrated to about 4 l. Determination of the content by evaporation of a portion resulted in a converted yield of 1.306 kg (96.4% of theory). The solution was used directly in the subsequent stage.

HPLC method A: RT about 11.9 min.

MS (EIpos): m/z=245 $[M+H]^+$ $^1H$ NMR (400 MHz, $CD_2Cl_2$): δ=3.84 (s, 3H), 3.90 (s, 3H), 7.12-7.20 (m, 2H), 7.62 (d, 1H).

Example 2

4-Bromo-2-methoxybenzaldehyde (XIX)

(XIX)

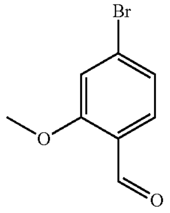

1.936 kg (6.22 mol) of a 65% Red-Al solution in toluene were charged with 1.25 l of toluene at −5° C. To this solution was added 0.66 kg (6.59 mol) of 1-methylpiperazine, which was rinsed in with 150 ml of toluene, keeping the temperature between −7 and −5° C. The mixture was then left to stir at 0° C. for 30 minutes. This solution was then added to a solution of 1.261 kg (5.147 mol) of methyl 4-bromo-2-methoxybenzoate (XV), dissolved in 4 l of toluene, keeping the temperature at −8 to 0° C. After rinsing in twice with 0.7 l of toluene, the mixture was then stirred at 0° C. for 1.5 hours. For the work-up, the solution was added to cold aqueous sulphuric acid at 0° C. (12.5 l of water+1.4 kg of conc. sulphuric acid). The temperature should increase at maximum to 10° C. (slow addition). The pH was adjusted to pH 1, if necessary, by addition of further sulphuric acid. The organic phase was separated off and the aqueous phase was extracted with 7.6 l of toluene. The combined organic phases were washed with 5.1 l of water and then substantially concentrated and the residue taken up in 10 l of DMF. The solution was again concentrated to a volume of about 5 l. Determination of the content by evaporation of a portion resulted in a converted yield of 1.041 kg (94.1% of theory). The solution was used directly in the subsequent stage.

HPLC method A: RT about 12.1 min.

MS (EIpos): m/z=162 $[M+H]^+$ $^1$H NMR ($CDCl_3$, 400 MHz): δ=3.93 (3H, s), 7.17 (2H, m), 7.68 (1H, d), 10.40 (1H, s)

Example 3

4-Formyl-3-methoxybenzonitrile (VI)

VI

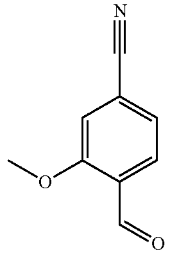

719 g (3.34 mol) of 4-bromo-2-methoxybenzaldehyde (XVI) as a solution in 4.5 l of DMF were charged with 313 g (0.74 mol) of potassium hexacyanoferrate ($K_4[Fe(CN)_6]$) and 354 g (3.34 mol) of sodium carbonate and a further 1.2 l of DMF and 3.8 g (0.017 mol) of palladium acetate were added. The mixture was stirred at 120° C. for 3 hours. The mixture was left to cool to 20° C. and 5.7 l of water were added to the mixture. The mixture was extracted with 17 l of ethyl acetate and the aqueous phase was washed once more with 17 l of ethyl acetate. The organic phases were combined and substantially concentrated, taken up in 5 l of isopropanol and concentrated to about 2 l. The mixture was heated to boiling and 2 l of water were added dropwise. The mixture was allowed to cool to 50° C. and another 2 l of water were added. The mixture was cooled to 3° C. and stirred at this temperature for one hour. The product was filtered off and washed with water (2×1.2 l). The product was dried at 40° C. under vacuum.

Yield: 469 g (87% of theory) of a beige solid.

HPLC method A: RT about 8.3 min.

MS (EIpos): m/z=162 [M+H]+

1H NMR (300 MHz, DMSO-d6): δ=3.98 (s, 3H), 7.53 (d, 1H), 7.80 (s, 1H), 7.81 (d, 1H), 10.37 (s, 1H).

Example 4

(2E/2Z)-2-(4-Cyano-2-methoxybenzylidene)-3-oxobutanamide (XVI a,b)

XVI a+b

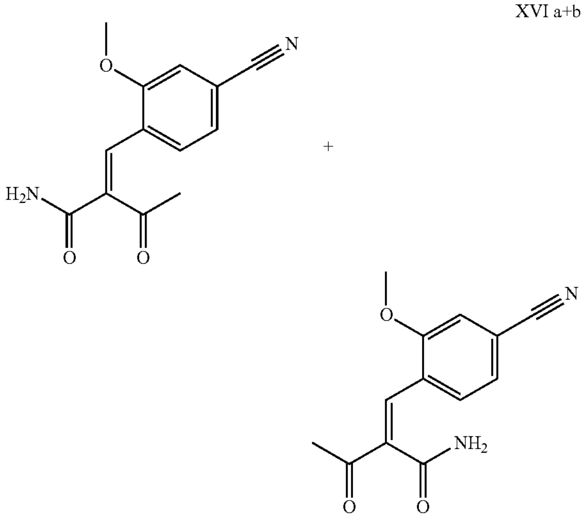

1000 g (6204.95 mmol) of 4-formyl-3-methoxybenzonitrile (VI), 721.5 g (7135.7 mmol) of 3-oxobutanamide (XVII), 53 g (620 mmol) of piperidine and 37.3 g (620 mmol) of glacial acetic acid were heated under reflux in 15 l of dichloromethane for 4 hours on a water separator. Subsequently, about 10 l of dichloromethane were distilled off and the mixture was left to cool to room temperature. The mixture was cooled to 0° C. and left to stir for 4 hours, and the product was filtered off and washed twice with 1000 ml each time of cold dichloromethane. The product was dried at 40° C. under vacuum under entraining gas.

Yield: 1439.8 g (95.0% of theory) of a yellow solid.

HPLC method A: RT about 3.55 min.

MS (EIpos): m/z=245 $[M+H]^+$ $^1$H NMR (500 MHz, DMSO-$d_6$): δ=2.35 (s, 3H), 3.30 (s, 2H), 3.90 (s, 3H), 7.45 (d, 1H), 7.7 (m, 3H), 7.75 (d, 1H), 8.85 (d, 1H)

Example 5

4-(4-Cyano-2-methoxyphenyl)-2,8-dimethyl-5-oxo-1,4,5,6-tetrahydro-1,6-naphthyridine-3-carboxamide (XVIII)

(XIII)

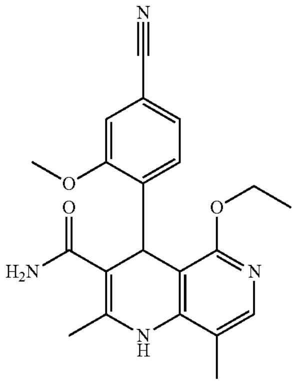

2.128 kg (8.712 mol) of (2E/2Z)-2-(4-cyano-2-methoxybenzylidene)-3-oxobutanamide (XVI a,b) were taken up with 29 l of 2-butanol, 1.277 kg (7.92 mol) of 4-amino-5-methylpyridone were added, and then the mixture was heated in a closed stirred tank under elevated pressure at internal temperature 120° C. for 12 h. The mixture was then cooled to 0° C. by means of a gradient over a period of 5 h and then stirred at 0° C. for 3 hours. The product was then filtered off and washed with 2.1 l of cold isopropanol. The product was dried at 60° C. under vacuum.

Yield: 2.081 kg (75% of theory based on 4-amino-5-methylpyridone, since this component is used substoichiometrically) of a pale yellow solid.

HPLC method A: RT about 3.64 min.

MS (EIpos): m/z=351 $[M+H]^+$ $^1$H NMR (500 MHz, DMSO-$d_6$): δ=2.00 (s, 3H), 2.10 (s, 3H), 3.78 (s, 3H), 5.22 (s, 1H), 6.65 (s(broad), 1H), 6.85 (s(broad), 1H), 6.91 (s, 1H), 7.11 (d, 1H), 7.28 (d, 1H), 7.35 (s, 1H), 7.52 (s, 1H), 10.61 (s, 1H)

Example 5

4-(4-Cyano-2-methoxyphenyl)-5-ethoxy-2,8-dimethyl-1,4-dihydro-1,6-naphthyridine-3-carboxamide (XIII)

(XIII)

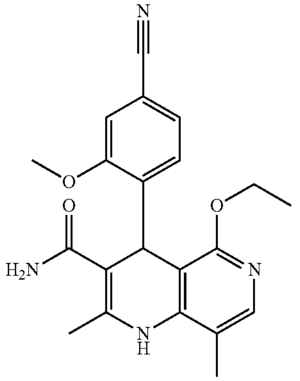

1.857 kg (5.3 mol) of 4-(4-cyano-2-methoxyphenyl)-2,8-dimethyl-5-oxo-1,4,5,6-tetrahydro-1,6-naphthyridine-3-carboxamide (XVIII) and 4.70 kg (29 mol) of triethyl orthoacetate were dissolved in 12.15 l of dimethylacetamide, and 157.5 g of concentrated sulphuric acid were added. The mixture was heated at 115° C. for 1.5 hours and then cooled to 50° C. At 50° C., 12.15 l of water were added dropwise over 30 minutes. After completion of the addition, the mixture was seeded with 10 g of the title compound (XI) and a further 12.15 l of water were added dropwise over 30 minutes at 50° C. The mixture was cooled to 0° C. (gradient, 2 hours) and then stirred at 0° C. for two hours. The product was filtered off, washed twice with 7.7 l each time of water and dried at 50° C. under vacuum.

Yield: 1.845 kg (92.0% of theory) of a pale yellow solid.

HPLC method B: RT about 10.2 min.

MS (EIpos): m/z=433 $[M+H]^+$ $^1$H NMR (300 MHz, DMSO-$d_6$): δ=1.11 (t, 3H), 2.16 (s, 3H), 2.42 (s, 3H), 2.78 (m, 2H), 3.77 (s, 3H), 4.01-4.13 (m, 4H), 5.37 (s, 1H), 7.25 (d, 1H), 7.28-7.33 (m, 2H), 7.60 (s, 1H), 8.35 (s, 1H).

Example 6

(4S)-4-(4-Cyano-2-methoxyphenyl)-5-ethoxy-2,8-dimethyl-1,4-dihydro-1,6-naphthyridine-3-carboxamide (I) as a Solution in 40:60 acetonitrile/methanol (I)

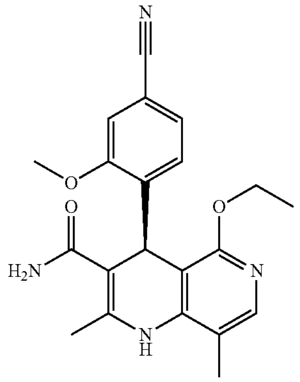

Enantiomer Separation on an SMB System

The feed solution was a solution corresponding to a concentration consisting of 50 g of racemic 4-(4-cyano-2-methoxyphenyl)-5-ethoxy-2,8-dimethyl-1,4-dihydro-1,6-naphthyridine-3-carboxamide (XIII), dissolved in 1 liter of a mixture of 60:40 methanol/acetonitrile.

The solution was chromatographed by means of an SMB system on a stationary phase: Chiralpak AS-V, 20 μm. The pressure was 30 bar and a mixture of methanol/acetonitrile 60:40 was used as eluent.

9.00 kg of 4-(4-cyano-2-methoxyphenyl)-5-ethoxy-2,8-dimethyl-1,4-dihydro-1,6-naphthyridine-3-carboxamide (XIII) were dissolved in 180 l of a mixture consisting of methanol/acetonitrile 60:40 and chromatographed by means of SMB. After concentrating the product-containing fractions, 69.68 liters of a 6.2% solution (corresponding to 4.32 kg of (4S)-4-(4-cyano-2-methoxyphenyl)-5-ethoxy-2,8-dimethyl-1,4-dihydro-1,6-naphthyridine-3-carboxamide (I)) were obtained as a solution in acetonitrile/methanol 40:60.

Yield: 4.32 kg (48% of theory), as a colourless fraction dissolved in 69.68 liters of acetonitrile/methanol 40:60.

Enantiomeric purity: >98.5% e.e. (HPLC, Method D)

A sample is concentrated under vacuum and gives: MS (EIpos): m/z=379 $[M+H]^+$ $^1H$ NMR (300 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 7

(4S)-4-(4-Cyano-2-methoxyphenyl)-5-ethoxy-2,8-dimethyl-1,4-dihydro-1,6-naphthyridine-3-carboxamide (I)

(I)

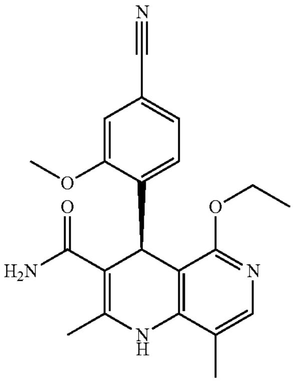

Crystallization and Polymorph Adjustment 64.52 liters of a 6.2% solution from Example 6 in a mixture of acetonitrile/methanol 40:60 (corresponding to 4.00 kg of compound 1) were filtered through a filter cartridge (1.2 um) and subsequently sufficiently concentrated at 250 mbar such that the solution was still stirrable. 48 l of ethanol, denatured with toluene, was added and distilled again at 250 mbar up to the limit of stirrability (redistillation in ethanol). A further 48 l of ethanol, denatured with toluene, were added and then distilled off at atmospheric pressure down to a total volume of about 14 l (jacket temperature 98° C.). The mixture was cooled via a gradient (4 hours) to 0° C., stirred at 0° C. for 2 hours and the product filtered off. The product was washed twice with 4 l of cold ethanol each time and then dried at 50° C. under vacuum.

Yield: 3.64 kg (91% of theory) of a colourless crystalline powder.

Enantiomeric purity: >>99% e.e. (HPLC Method D); retention times/RRT: (4S)-4-(4-cyano-2-me thoxyphenyl)-5-ethoxy-2,8-dimethyl-1,4-dihydro-1,6-naphthyridine-3-carboxamide (I) about 11 min. RRT: 1.00; (4R)-4-(4-cyano-2-methoxyphenyl)-5-ethoxy-2,8-dimethyl-1,4-dihydro-1,6-naphthyridine-3-carboxamide (I) about 9 min. RRT: 0.82

Purity: >99.8% (HPLC Method B), RT: about 6.7 min.

Content: 99.9% (relative to external standard)

specific rotation (chloroform, 589 nm, 19.7° C., c=0.38600 g/100 ml): −148.8°.

MS (EIpos): m/z=379 $[M+H]^+$ $^1H$ NMR (300 MHz, DMSO-$d_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Melting point: 252° C. (compound of the formula (I) in crystalline form of polymorph I)

Physicochemical Characterization of Compound of the Formula (I) in Crystalline Form of Polymorph I Compound of the formula (I) in crystalline form of polymorph I melts at 252° C., ΔH=95-113 $Jg^{-1}$ (heating rate 20 $Kmin^{-1}$).

A depression of the melting point was observed depending on the heating rate.

The melting point decreases at a lower heating rate (e.g. 2 $Kmin^{-1}$) since decomposition occurs.

No other phase transitions were observed. A loss of mass of about 0.1% was observed up to a temperature of 175° C.

Stability and Moisture Absorption

Samples of compound of the formula (I) in crystalline form of polymorph I were stored at 85% and 97% rel. humidity (25° C.). The samples were evaluated after 12 months by DSC, TGA and XRPD. After 12 months, a mass change of <0.1% is observed in both cases. This means that compound of the formula (I) in crystalline form of polymorph I shows no significant absorption of water under these storage conditions. According to DSC, TGA and XRPD, no difference exists in compound of the formula (I) in crystalline form of polymorph I.

HPLC Conditions/Methods

Method A

YMC Hydrosphere C18

150*4.6 mm, 3.0 μm

25° C., 1 ml/min, 270 nm, 4 nm

0': 70% TFA 0.1%*; 30% acetonitrile

17': 20% TFA 0.1%*; 80% acetonitrile

18': 70% TFA 0.1%*; 30% acetonitrile

*: TFA in water

Method B

YMC Hydrosphere C18

150*4.6 mm, 3.0 μm

25° C., 1 ml/min, 255 nm, 6 nm

0': 90% TFA 0.1%*; 10% acetonitrile

20': 10% TFA 0.1%*; 90% acetonitrile

18': 10% TFA 0.1%*; 90% acetonitrile

Method C

Nucleodur Gravity C18

150*2 mm, 3.0 μm

35° C., 0.22 ml/min, 255 nm, 6 nm

Solution A: 0.58 g of ammonium hydrogen phosphate and 0.66 g of ammonium dihydrogen phosphate in 1l of water (ammonium phosphate buffer pH 7.2)

Solution B: acetonitrile

0': 30% B; 70% A

15': 80% B; 20% A

25': 80% B; 20% A

Method D

Column length: 25 cm

Internal diameter: 4.6 mm

Packing: Chiralpak IA, 5 μm

Reagents: 1. Acetonitrile HPLC grade 2. Methyl tert-butyl ether (MTBE), p.a.

Test solution The sample is dissolved at a concentration of 1.0 mg/ml in acetonitrile.

(e.g. about 25 mg of sample, weighed accurately, dissolved in acetonitrile to 25.0 ml).

Eluent A. acetonitrile

B. Methyl tert-butyl ether (MTBE), p.a.

Flow rate 0.8 ml/min

Column oven temperature 25° C.

Detection measurement wavelength: 255 nm

Bandwidth: 6 nm

Injection volumes 5 μl

Mix composition of eluents A and B in ratio by volume of 90:10

Chromatogram run time 30 min

Retention times/RRT:

(4S)-4-(4-cyano-2-methoxyphenyl)-5-ethoxy-2,8-dimethyl-1,4-dihydro-1,6-naphthyridine-3-carboxamide (1) about 11 min. RRT: 1.00

(4R)-4-(4-cyano-2-methoxyphenyl)-5-ethoxy-2,8-dimethyl-1,4-dihydro-1,6-naphthyridine-3-carboxamide (1) about 9 min. RRT: 0.82

Measuring Parameters of the X-Ray Diffractometry for the Analysis of the Compound of the Formula (I) in Crystalline Form of Polymorph I

| | |
|---|---|
| Dataset name | 2429-08a r2 |
| Scan axis | 2Theta-Omega |
| Start position [°2th.] | 2.0000 |
| End position [°2th.] | 37.9900 |
| Type of divergence slit | fixed |
| Size of divergence slit [°] | 1.0000 |
| Measurement temperature [° C.] | 25 |
| Anode material | Cu |
| K-alpha1 [Å] | 1.54060 |
| Generator setting | 35 mA, 45 kV |
| Diffractometer type | transmission diffractometer |
| Goniometer radius [mm] | 240.00 |
| Focus-div. slit gap [mm] | 91.00 |
| Primary beam monochromator | yes |
| Sample rotation | yes |

| Peak maximum [2 theta] Polymorph I |
|---|
| 8.5 |
| 11.4 |
| 11.9 |
| 13.4 |
| 14.1 |
| 14.8 |
| 15.0 |
| 15.4 |
| 16.0 |
| 17.2 |
| 18.5 |
| 19.0 |
| 19.8 |
| 20.5 |
| 20.8 |
| 22.1 |
| 22.7 |
| 23.0 |
| 23.1 |
| 23.6 |
| 23.9 |
| 24.6 |
| 24.9 |
| 25.2 |
| 25.6 |
| 26.0 |
| 26.5 |
| 27.1 |
| 27.3 |
| 28.3 |
| 28.5 |
| 28.8 |
| 29.6 |
| 30.1 |
| 30.6 |
| 31.5 |
| 31.9 |
| 32.4 |
| 32.9 |
| 33.1 |
| 33.4 |
| 33.7 |
| 34.5 |
| 34.7 |
| 35.0 |
| 35.8 |
| 36.2 |
| 36.5 |

-continued

| |
|---|
| 37.2 |
| 37.4 |

Measuring Conditions for the IR and Raman Spectroscopy for the Measurement of the Compound of the Formula (I) in Crystalline Form of Polymorph I:

| IR: | |
|---|---|
| Instrument | Perkin Elmer Spectrum One |
| Number of scans | 32 |
| Resolution | 4 $cm^{-1}$ |
| Technique | Diamond ATR unit |
| **Raman:** | |
| Instrument | Bruker Raman RFS 100/S |
| Number of scans | 64 |
| Resolution | 2-4 $cm^{-1}$ |
| Laser power | 350 mW |
| Laser wavelength | 1064 nm |

| Band maximum [$cm^{-1}$] | |
|---|---|
| IR-ATR Polymorph I | Raman Polymorph 1 |
| 3475 | 3074 |
| 3416 | 2997 |
| 3366 | 2970 |
| 3074 | 2941 |
| 2992 | 2920 |
| 2952 | 2836 |
| 2835 | 2231 |
| 2230 | 1659 |
| 1681 | 1641 |
| 1658 | 1623 |
| 1606 | 1601 |
| 1572 | 1577 |
| 1485 | 1487 |
| 1464 | 1443 |
| 1454 | 1383 |
| 1431 | 1362 |
| 1420 | 1327 |
| 1407 | 1303 |
| 1381 | 1267 |
| 1355 | 1230 |
| 1341 | 1191 |
| 1325 | 1161 |
| 1303 | 1123 |
| 1285 | 1093 |
| 1267 | 1032 |
| 1255 | 991 |
| 1229 | 883 |
| 1222 | 827 |
| 1161 | 810 |
| 1136 | 759 |
| 1097 | 734 |
| 1031 | 708 |
| 991 | 671 |
| 976 | 613 |
| 967 | 528 |
| 924 | 505 |
| 909 | 471 |
| 875 | 442 |
| 847 | 346 |
| 827 | 320 |
| 810 | 297 |
| 776 | 186 |
| 758 | 155 |
| 746 | 114 |
| 733 | |
| 723 | |
| 706 | |
| 697 | |
| 670 | |

The invention claimed is:

1. A process for preparing a compound of the formula (I)

(I)

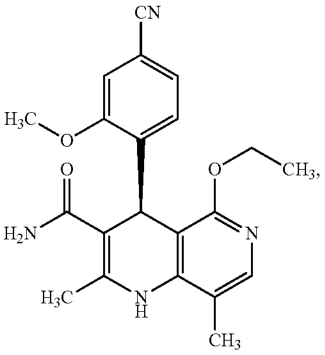

comprising separating a racemic compound of the formula (XIII) into its enantiomers, wherein the compound of the formula (XIII)

XIII

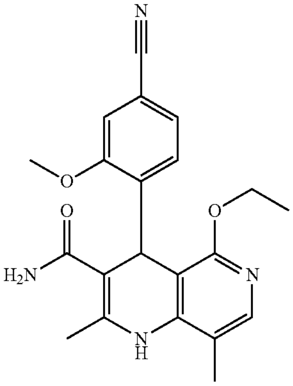

, is prepared by reacting a compound of the formula (XVIII)

XVIII

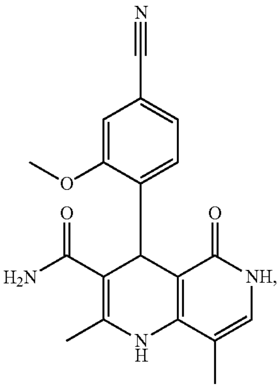

with an orthoester (XX)

(XX)

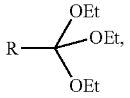

where R may be H or methyl, wherein the compound of the formula (XVIII)

(XVIII)

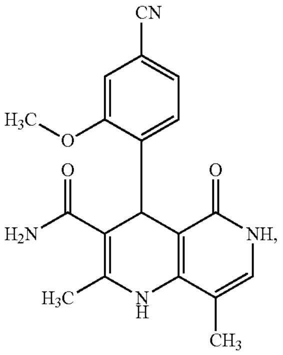

is prepared by reacting compounds of the formula (XVI a,b)

XVI a + b

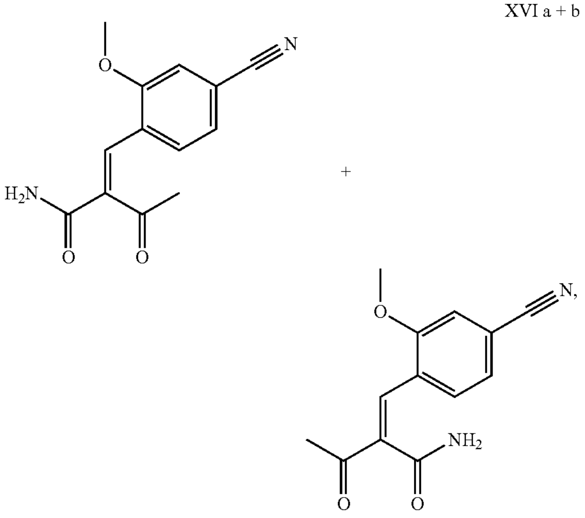

with a compound of the formula (IX)

IX

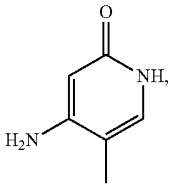

and wherein the compound of the formula (XVI a,b) is prepared by reacting a compound of the formula (VI)

VI

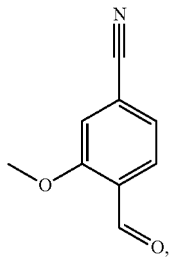

with a compound of the formula (XVII)

(XVII)

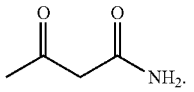

2. A process for preparing a compound of the formula (I)

(I)

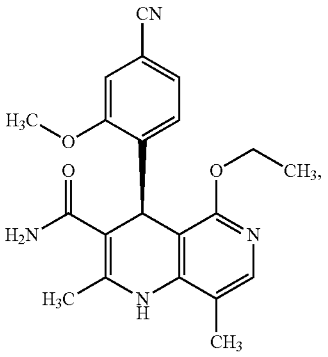

comprising separating a racemic compound of the formula (XIII) into its enantiomers, where the compound of the formula (XIII)

XIII

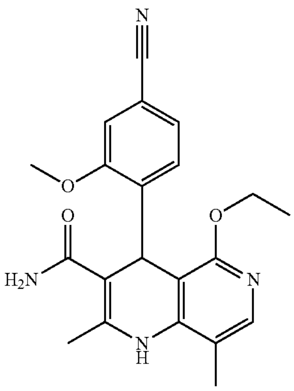

, is prepared by reacting a compound of the formula (XVIII)

XVIII

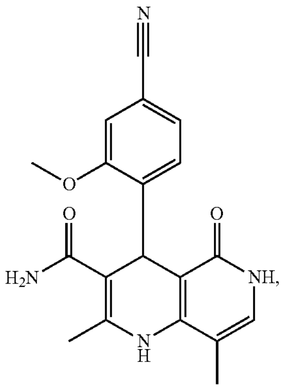

with an orthoester (XX)

(XX)

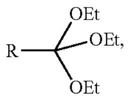

where R may be H or methyl, and wherein the compound of the formula (XVIII)

(XVIII)

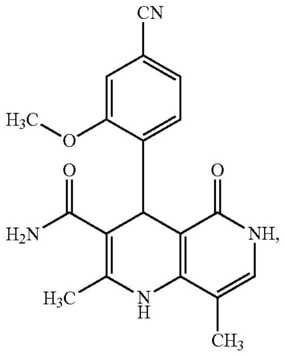

is prepared by reacting compounds of the formula (XVI a,b)

XVI a + b

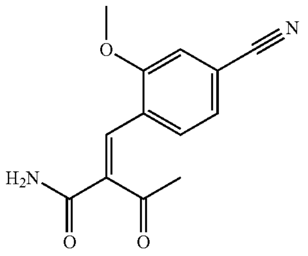

+

-continued

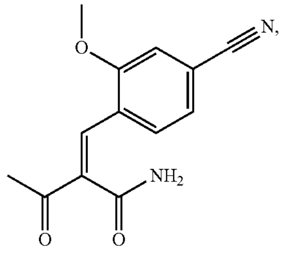

with a compound of the formula (IX)

IX

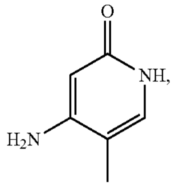

3. A process for preparing a compound of the formula (I)

(I)

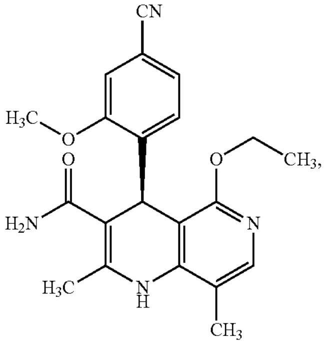

comprising separating a racemic compound of the formula (XIII) into its enantiomers, where the compound of the formula (XIII)

XIII

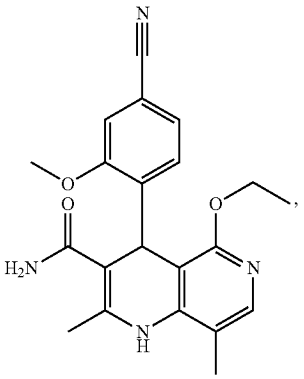

is prepared by reacting a compound of the formula (XVIII)

XVIII

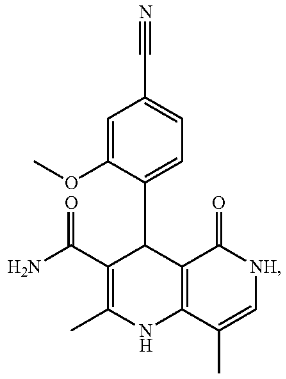

with an orthoester (XX)

(XX)

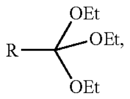

where R may be H or methyl.

4. A process for preparing a compound of the formula (I)

(I)

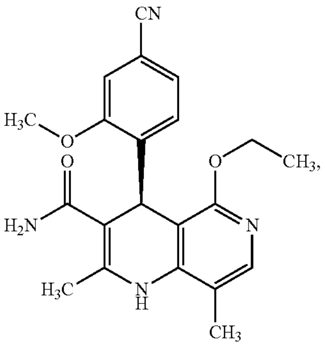

comprising using the compound of the formula (XVIII)

(XVIII)

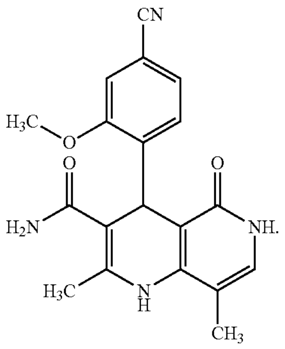

5. A process for preparing a compound of the formula (I)

(I)

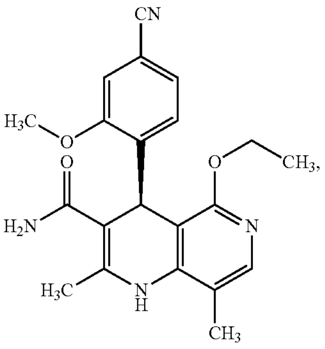

comprising using the compounds of the formula (XVI a,b)

XVI a+b

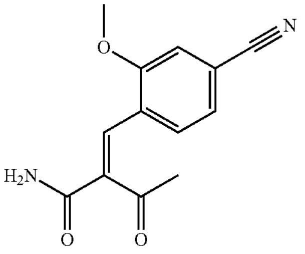

+

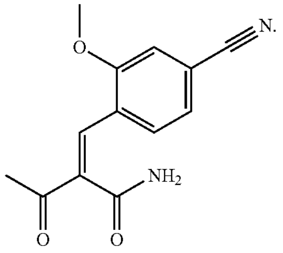

6. A process for preparing a compound of the formula (I)

(I)

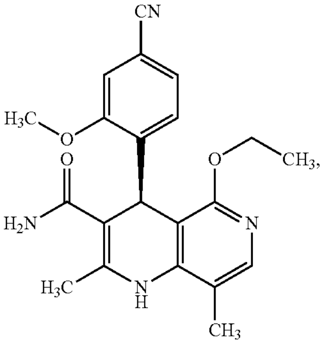

comprising using a compound of the formula (XVIII)

(XVIII)

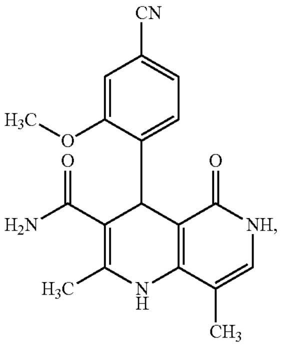

and compounds of the formula (XVI a,b)

XVI a+b

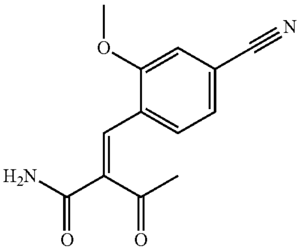

+

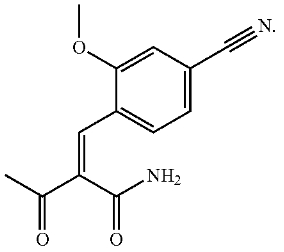

7. A compound of the formula (XVIII)

(XVIII)

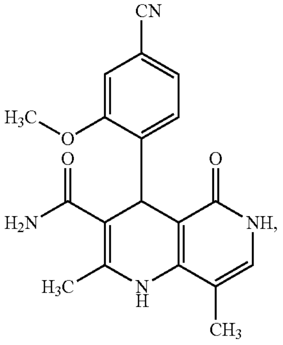

and the salts, solvates and solvates of the salts thereof.

8. A compound of the formula (XVI a,b) as an E/Z mixture

XVI a+b

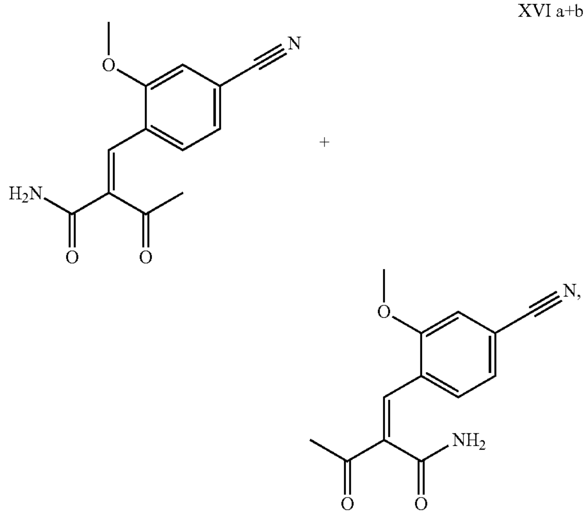

and the salts, solvates and solvates of the salts thereof.

9. A process for preparing a compound of the formula (XVIII)

(XVIII)

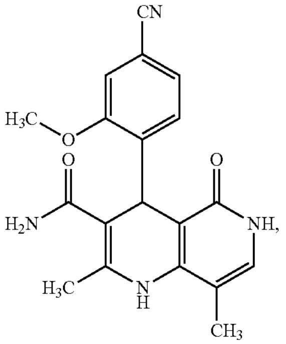

comprising reacting compounds of the formula (XVI a,b)

XVI a+b

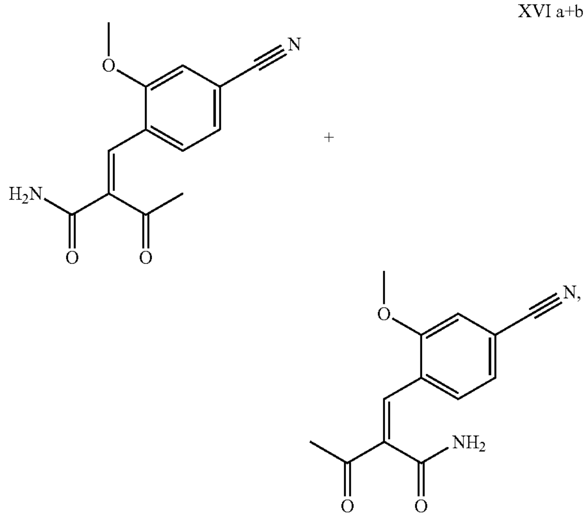

with a compound of the formula (IX)

IX

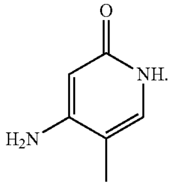

10. A process for preparing compounds of the formula (XVI a,b)

XVI a+b

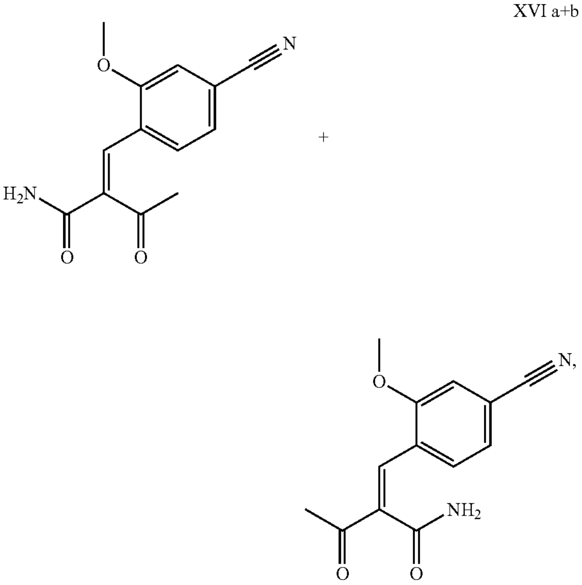 [SMILES: COc1cc(C#N)ccc1/C=C(\C(C)=O)C(N)=O ; COc1cc(C#N)ccc1/C=C(/C(C)=O)C(N)=O]

comprising reacting a compound of the formula (VI)

VI

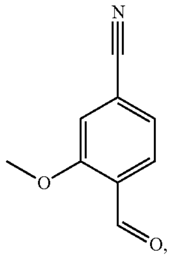

with a compound of the formula (XVII)

(XVII)

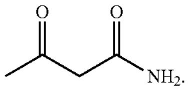

11. A process for preparing a compound of the formula (XIII)

XIII

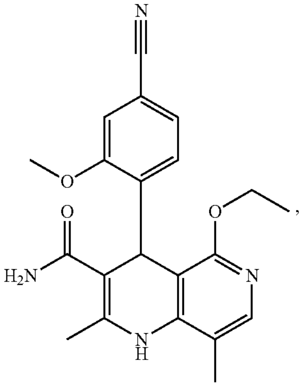

comprising reacting a compound of the formula (XVIII)

(XVIII)

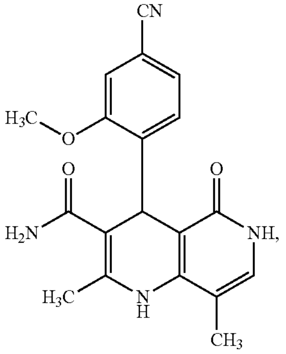

with an orthoester (XX)

(XX)

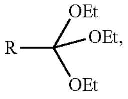

where R may be H or methyl.

12. A process for preparing a compound of the formula (XIII)

XIII

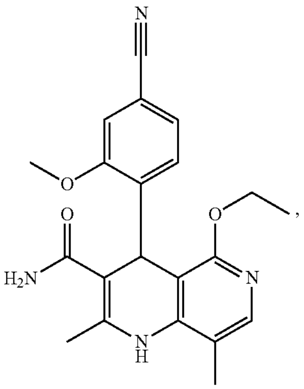

comprising reacting a compound of the formula (XVIII)

(XVIII)

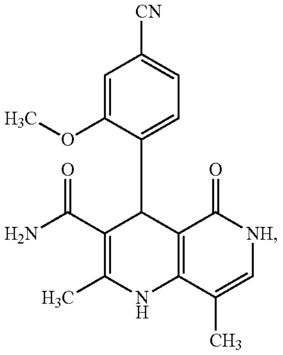

with an orthoester (XX)

(XX)

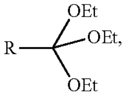

where R may be H or methyl, and wherein the compound of the formula (XVIII) is prepared by reacting compounds of the formula (XVI a,b)

XVI a+b

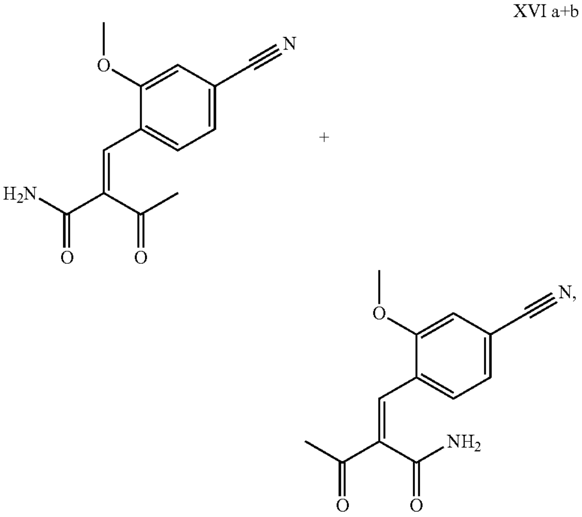

with a compound of the formula (IX)

IX

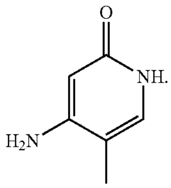

13. A process for preparing a compound of the formula (I) in crystalline polymorph I
(I)
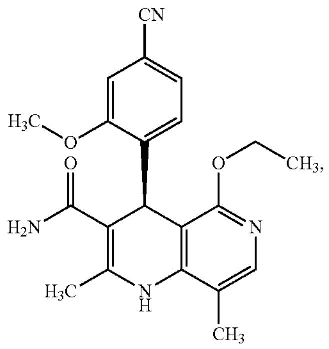
comprising preparing a compound of the formula (I)
(I)
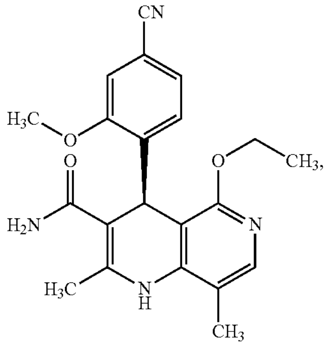
according to claim 1 and then stirring the compound of the formula (I), present in one or more polymorphs or as a solvate in an inert solvent, at a temperature of 20° C.-120° C. and isolating the compound of the formula (I) in crystalline polymorph I.
* * * * *